US012807989B2

(12) United States Patent
Morley

(10) Patent No.: US 12,807,989 B2
(45) Date of Patent: Nov. 24, 2026

(54) AMPLIFICATION METHOD

(71) Applicant: Monoquant Pty Ltd., Adelaide (AU)

(72) Inventor: Alexander Alan Morley, Toorak (AU)

(73) Assignee: Monoquant Pty Ltd., Adelaide (AU)

( * ) Notice: Subject to any disclaimer, the term of this patent is extended or adjusted under 35 U.S.C. 154(b) by 0 days.

(21) Appl. No.: 16/478,666

(22) PCT Filed: Jun. 7, 2019

(86) PCT No.: PCT/AU2019/050590
§ 371 (c)(1),
(2) Date: Jul. 17, 2019

(87) PCT Pub. No.: WO2019/237145
PCT Pub. Date: Dec. 19, 2019

(65) Prior Publication Data

US 2022/0098655 A1 Mar. 31, 2022

Related U.S. Application Data

(60) Provisional application No. 62/683,415, filed on Jun. 11, 2018, provisional application No. 62/757,634, filed on Nov. 8, 2018.

(51) Int. Cl.
*C12Q 1/6858* (2018.01)
*C12Q 1/6853* (2018.01)
*C12Q 1/6881* (2018.01)
*C12Q 1/6886* (2018.01)

(52) U.S. Cl.
CPC ......... *C12Q 1/6858* (2013.01); *C12Q 1/6853* (2013.01); *C12Q 1/6881* (2013.01); *C12Q 1/6886* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2009/0209432 A1 * 8/2009 Morley .................. C07H 21/04 506/17

FOREIGN PATENT DOCUMENTS

| | | | |
|---|---|---|---|
| CN | 1806051 A | 7/2006 | |
| CN | 1965089 A | 5/2007 | |
| WO | WO 2013/086450 | 6/2013 | |
| WO | WO 2013/086450 A1 | 6/2013 | |
| WO | WO 2018/005983 | 1/2018 | |
| WO | WO-2018005983 A1 * | 1/2018 | ........... C12Q 1/6827 |

OTHER PUBLICATIONS

Brisco, Determining the Repertoire of IGH Gene Rearrangements to Develop Molecular Markers for Minimal Residual Disease in B-Lineage Acute Lymphoblastic Leukemia, Journal of Molecular Diagnostics, 11(3): 194-200, 2009. (Year: 2009).*

Poritz, Getting Things Backwards to Prevent Primer Dimers, J. Molecular Diagnostics, 16(2): 159-162, 2014. (Year: 2014).*

Dufour, Annika et al., "Assessment of Minimal Residual Disease (MRD) in Relapsed CLL Patients Treated with Fludarabine and Cyclophosphamide with or without Rituximab (REACH)" Blood, 2010, p. 1390, vol. 116, No. 21.

Li, Aihong et al., "Sequence analysis of clonal immunoglobulin and T-cell receptor gene rearrangements in children with acute lymphoblastic leukemia at diagnosis and at relapse: implications for pathogenesis and for the clinical utility of PCR-based methods of minimal residual disease detection" Blood, Dec 2003, pp. 4520-4526, vol. 102, No. 13.

Morley, Alexander A. et al., "High-Annealing-Temperature PCR (HAT-PCR) Enables Sensitive Quantification of Minimal Residual Disease (MRD) in Blood in Acute Lymphoblastic Leukaemia (ALL)" Blood, 2018, p. 2831, vol. 132, Supplement 1.

Van Dongen, JJM et al., "Design and standardization of PCR primers and protocols for detection of clonal immunoglobulin and T-cell receptor gene recombinations in suspect lymphoproliferations: Report of the BIOMED-2 Concerted Action BMH4-CT98-3936" Leukemia, 2003, pp. 2257-2317, vol. 17.

Yang, Xiao Yan et al., "Rapid Detection of Clonal T-Cell Receptor-B Gene Rearrangements in T-Cell Lymphomas Using the LightCycier-Polymerase Chain Reaction with DNA Melting Curve Analysis" Journal of Molecular Diagnostics, Feb. 2005, pp. 81-88, vol. 7, No. 1.

Supplementary European Search Report for EP 19820379 issued Mar. 30, 2022.

(Continued)

*Primary Examiner* — Gary Benzion
*Assistant Examiner* — Carolyn L Greene
(74) *Attorney, Agent, or Firm* — Knobbe, Martens, Olson & Bear, LLP

(57) ABSTRACT

The present invention relates generally to an improved method of amplifying a nucleic acid region of interest and to primers for use therein. More particularly, the present invention is directed to an improved method of amplifying a nucleic acid region which has resulted from the recombination of two or more immunoglobulin or T cell receptor gene segments and primers for use therein. The method of the present invention is based on the determination that performing the amplification step using primers which exhibit a high Tm and/or using a high annealing temperature enables higher levels of sensitivity than has previously been achievable in the context of prior art methods of amplifying rearranged immunological or T cell receptor genes. Still further improvements in sensitivity are achievable where the subject primer hybridises to at least two N regions of the recombined gene. The provision of a highly sensitive yet simple means of detecting specific immunological and T cell receptor nucleic acid recombination events is useful in a range of applications including, but not limited to, the diagnosis and/or monitoring of clonal lymphoid cell populations or disease conditions which are characterised by specific V/D/J recombination events (such as detecting minimal residual disease in leukaemias) or the analysis or identification of immunological or T cell receptor gene regions of interest.

27 Claims, 4 Drawing Sheets

Specification includes a Sequence Listing.

(56) References Cited

OTHER PUBLICATIONS

Brisco, Michael J. et al., "Antisense Pcr: A simple and robust method for performing nested single-tube PCR" Analytical Biochemistry, 2011, pp. 176-182, vol. 409.

Brüggemann, M. et al., "Rearranged T-cell receptor beta genes represent powerful targets for quantification of minimal residual disease in childhood and adult T-cell acute lymphoblastic leukemia" Leukemia, 2004, pp. 709-719, vol. 18.

Ladetto, M. et al., "Next-generation sequencing and real-time quantitative PCR for minimal residual disease detection in B-cell disorders" Leukemia, 2014, pp. 1299-1307, vol. 28.

Mecklenburg, Michael W. "Design of High-Annealing-Temperature PCR Primers and Their Use in the Development of a Versatile Low-Copy-Number Amplification Protocol" Advances in Molecular and Cell Biology, 1996, pp. 473-490, vol. 15B.

Moreley, Alexander A. et al., "Sensitive and Specific Measurement of Minimal Residual Disease in Acute Lymphoblastic Leukemia" Journal of Molecular Diagnostics, May 2009, pp. 201-210, vol. 11, No. 3.

Moreley, Alexander A. et al., "High-Annealing-Temperature PCR (HAT-PCR) Enables Sensitive Quantification of Minimal Residual Disease (MRD) in Blood in Acute Lymphoblastic Leukaemia (ALL)" Blood, 2018, vol. 132, Supplement 1, 2831.

Nakao, Makoto et al., "Rapid and Reliable Quantification of Minimal Residual Disease in Acute Lymphoblastic Leukemia Using Rearranged Immunoglobulin and T-Cell Receptor Loci by LightCycler Technology" Cancer Research, Jun. 200, pp. 3281-3289, vol. 60.

Pongers-Willemse, MJ et al., "Primers and protocols for standardized detection of minimal residual disease in acute lymphoblastic leukemia using immunoglobulin and T cell receptor gene rearrangements and TAL1 deletions as PCR targets" Leukemia, 1999, pp. 110-118, vol. 13.

Puig, N. et al., "Critical evaluation of ASO RQ-PCR for minimal residual disease evaluation in multiple myeloma. A comparative analysis with flow cytometry" Leukemia, 2014, pp. 391-397, vol. 28.

Van Der Velden, VHJ et al., "Immunoglobulin kappa deleting element rearrangements in precursor-B acute lymphoblastic leukemia are stable targets for detection of minimal residual disease by real-time quantitative PCR" Leukemia, 2002, pp. 928-936, vol. 16.

Van Der Velden, VHJ et al., "T cell receptor gamma gene rearrangements as targets for detection of minimal residual disease in acute lymphoblastic leukemia by real-time quantitative PCR analysis" Leukemia, 2002, pp. 1372-1380, vol. 16.

Van Der Velden, VHJ et al., "Detection of minimal residual disease in acute leukemia" Journal of Biological Regulators and Homeostatic Agents, 2004, pp. 146-154, vol. 18, No. 2.

Van Der Velden, VHJ et al., "Optimization of PCR-based minimal residual disease diagnostics for childhood acute lymphoblastic leukemia in a multi-center setting" Leukemia, 2007, pp. 706-713, vol. 21.

Van Der Velden, VHJ et al., "MRD Detection in Acute Lymphoblastic Leukemia Patients Using Ig/TCR Gene Rearrangements as Targets for Real-Time Quantitative PCR" Methods in Molecular Biology, 2009, pp. 115-150, vol. 538.

Van Der Velden, VHJ et al., "Minimal residual disease diagnostics in acute lymphoblastic leukaemia: impact of primer characteristics and size of junctional regions" British Journal of Haematology, 2014, pp. 451-464, vol. 164.

Van Dongen, Jacques J.M. et al. "Minimal residual disease diagnostics in acute lymphoblastic leukemia: need for sensitive, fast, and standardized technologies" Blood, Jun. 2015, pp. 3996-4009, vol. 125, No. 26.

Verhagen, Ojhm et al., "Application of germline IGH probes in real-time quantitative PCR for the detection of minimal residual disease in acute lymphoblastic leukemia" Leukemia, 2000, pp. 1426-1435, vol. 14.

International Search Report for PCT/AU2019/050590 dated Sep. 13, 2019.

Li Xinquan. (1993) Pediatrics, Journal of External Medicine, vol. 20, No. 4, p. 191-194.

Van Belzen N, Hupkes PE, Doekharan D, Hoogeveen-Westerveld M, Dorssers LC, Van't Veer MB. Detection of minimal disease using rearranged immunoglobulin heavy chain genes from intermediate- and high-grade malignant B cell non-Hodgkins lymphoma. Leukemia. Oct. 1997;11(10):1742-52. doi: 10.1038/sj.leu.2400797. PMID: 9324296.

Aubin J, Davi F, Nguyen-Salomon F, et al. Description of a novel FR1 IgH PCR strategy and its comparison with three other strategies for the detection of clonality in B cell malignancies. Leukemia. Mar. 1995;9(3):471-479. PMID: 7533868.

Owczarzy R, You Y, Moreira BG, Manthey JA, Huang L, Behlke MA, Walder JA. Effects of sodium ions on DNA duplex oligomers: improved predictions of melting temperatures. Biochemistry. Mar. 30, 2004;43(12):3537-54. doi: 10.1021/bi034621r. PMID: 15035624.

Saygin C, Cannova J, Stock W, Muffly L. Measurable residual disease in acute lymphoblastic leukemia: methods and clinical context in adult patients. Haematologica. Dec. 1, 2022;107(12):2783-2793. doi: 10.3324/haematol.2022.280638. PMID: 36453516; PMCID: PMC9713546.

Chan DW, Liang R, Kwong YL, Chan V. Detection of T-cell receptor delta gene rearrangement in T-cell malignancies by clonal specific polymerase chain reaction and its application to detect minimal residual disease. Am J Hematol. Jul. 1996;52(3):171-7. doi: 10.1002/(SICI)1096-8652(Jul. 1996)52:3<171::AID-AJH6>3.0.CO;2-Q. PMID: 8756082.

Latham S, Hughes E, Budgen B, Ross D, Greenwood M, Bradstock K, Dalla-Pozza L, Huang L, Law T, Doculara L, Venn N, Ullah S, Sutton R, Morley AA. Sensitive Measurement of Minimal Residual Disease in Blood by HAT-PCR. J Mol Diagn. Jun. 2022;24(6):632-641. doi: 10.1016/j.jmoldx.2022.03.007. Epub Apr. 14, 2022. PMID: 35430373.

* cited by examiner

FIGURE 1

| SEQ ID NO | primer | sequence [illegible] | Tm | DD | Pbl | DD | Pbl | DD | Pbl | DD | Pbl |
|---|---|---|---|---|---|---|---|---|---|---|---|
| | | 45 cycles at 68°C-75°C | | 75 | 74.6 | 73.9 | 72.5 | 70.8 | 69.4 | 68.5 | 68 |
| 58 | 37/18single 1 | GACTGGTTATTAACTCACCTGGCATTTTGTGTTGAA | 71 | 33.37 | NA | 33.07 | NA | 33.02 | NA | 32.59 | NA |
| 59 | 37/18single 2 | CTGCTCTTGTTGGACCAGGGGTT | 69.8 | 33.81 | NA | 33.58 | NA | 33.57 | NA | 33.47 | NA |
| 60 | 37/18single 3 | GGATATTGTAGTAGTACCAGCTGCTGCTCTTGTT | 70.9 | 34.31 | NA | 31.96 | NA | 32.48 | 38.27/0 | 32.82 | NA |

AMPLIFICATION METHOD

CROSS REFERENCE TO RELATED APPLICATIONS

This application is a U.S. National Phase Application of PCT International Application Number PCT/AU2019/050590, filed on Jun. 7, 2019, designating the United States of America and published in the English language, which is an International Application of and claims the benefit of priority to U.S. Provisional Patent Application No. 62/757,634, filed on Nov. 8, 2018 and U.S. Provisional Application No. 62/683,415, filed on Jun. 11, 2018. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-WMRK6-005APC.txt, the date of creation of the ASCII text file is Jul. 17, 2019, and the size of the ASCII text file is 4 KB.

FIELD OF THE INVENTION

The present invention relates generally to an improved method of amplifying a nucleic acid region of interest and to primers for use therein. More particularly, the present invention is directed to an improved method of amplifying a nucleic acid region which has resulted from the recombination of two or more immunoglobulin or T cell receptor gene segments and primers for use therein. The method of the present invention is based on the determination that performing the amplification step using primers which exhibit a high Tm and/or using a high annealing temperature enables higher levels of sensitivity than has previously been achievable in the context of prior art methods of amplifying rearranged immunological or T cell receptor genes. Still further improvements in sensitivity are achievable where the subject primer hybridises to at least two N regions of the recombined gene. The provision of a highly sensitive yet simple means of detecting specific immunological and T cell receptor nucleic acid recombination events is useful in a range of applications including, but not limited to, the diagnosis and/or monitoring of clonal lymphoid cell populations or disease conditions which are characterised by specific V/D/J recombination events (such as detecting minimal residual disease in leukaemias) or the analysis or identification of immunological or T cell receptor gene regions of interest.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Bibliographic details of the publications referred to by author in this specification are collected alphabetically at the end of the description.

A clone is generally understood as a population of cells which has descended from a common precursor cell. Diagnosis and/or detection of the existence of a clonal population of cells or organisms in a subject has generally constituted a relatively problematic procedure. Specifically, a clonal population may constitute only a minor component within a larger population of cells or organisms. For example, in terms of the mammalian organism, one of the more common situations in which detection of a clonal population of cells is required occurs in terms of the diagnosis and/or detection of neoplasms, such as cancer. However, detection of one or more clonal populations may also be important in the diagnosis of conditions such as myelodysplasia or polycythaemia vera and also in the detection of antigen driven clones generated by the immune system.

Generally, the population within which the clone arises corresponds to a population of cells within a particular tissue or compartment of the body. Nevertheless, despite the fact that sampling such a population of cells effectively narrows the examination to a sub group of cells or organisms, this may nevertheless still present a clinician with a large background population of non-clonal cells or organisms within which the clonal population must be identified.

If the members of the clone are characterized by a molecular marker, such as an altered sequence of DNA, then the problem of detection may be able to be translated into the problem of detecting a population of molecules which all have the same molecular sequence within a larger population of molecules which have a different sequence, either all being the same and different, or being heterogeneous to a greater or lesser extent. The level of detection of the marker molecules that can be achieved is very dependent upon the sensitivity and specificity of the detection method, but nearly always, when the proportion of target molecules within the larger population of molecules becomes small, the signal noise from the larger population makes it impossible to detect the signal from the target molecules.

A specific class of molecular markers which, although highly specific, present unique complexities in terms of its detection are those which result from genetic recombination events.

Recombination of the genetic material in somatic cells involves the bringing together of two or more regions of the genome which are initially separate. It may occur as a random process but it also occurs as part of the developmental process in normal lymphoid cells.

In relation to cancer, recombination may be simple or complex. A simple recombination may be regarded as one in which two unrelated genes or regions are brought into apposition. A complex recombination may be regarded as one in which more than two genes or gene segments are recombined. The classical example of a complex recombination is the rearrangement of the immunoglobulin (Ig) and T-cell receptor (TCR) variable genes which occurs during normal development of lymphoid cells and which involves recombination of the V, D and J gene segments. The loci for these gene segments are widely separated in the germline but recombination during lymphoid development results in apposition of V, D and J gene segments, or V and J gene segments, with the junctions between these gene segments being characterised by small regions of insertion and deletion of nucleotides ($N_1$ and $N_2$ regions). This process occurs randomly so that each normal lymphocyte comes to bear a unique V(D)J rearrangement which may be a complete VDJ rearrangement or a VJ or DJ rearrangement, depending both on the gene which is rearranged and on the nature of the rearrangement. Since a lymphoid cancer, such as acute lymphoblastic leukaemia, chronic lymphocytic leukaemia, lymphoma or myeloma, occurs as the result of neoplastic change in a single normal cell, all of the cancer cells will, at least originally, bear the junctional V(D)J rearrangement originally present in the founder cell. Subclones may arise during expansion of the neoplastic population and further V(D)J rearrangements may occur in them.

The unique DNA sequences resulting from recombination and which are present in a cancer clone or subclone provide a unique genetic marker which can be used to monitor the response to treatment and to make decisions on therapy. Monitoring of the clone can be performed by PCR, flow cytometry or next-gen sequencing. Monitoring by flow cytometry involves the determination of the immunophenotype of the cancer cells at diagnosis and searching for the same phenotype in subsequent samples in order to detect and quantify the cancer cells. Next-gen sequencing is a newer approach, the strengths and weaknesses of which are still being evaluated. However, this is also a costly technique.

PCR-based analysis is a preferred method due to its potentially high level of specificity and automation. Quantification by PCR conventionally involves sequencing of the marker rearrangement using DNA from a sample taken at the time of diagnosis, synthesis of patient-specific primers and use of these primers in a PCR on DNA extracted from samples obtained during treatment. Usually, two primers are placed on either side of the site of recombination, typically with the downstream primer being directed to the J gene segment and the upstream primer (which is also known as the allele specific oligonucleotide [ASO], being designed to be directed to the most variable region of the rearrangement (Bruggemann et al, 2004; Pongers-Willemse et al, 1999; Nakao et al, 2000; van der Velden et al, 2002; van der Velden et al, 2004; van der Velden et al, 2007; van der Velden et al, 2009; van der Velden et al, 2014; Verhagen et al, 2000). Occasionally the upstream primer is directed to the V gene segment and the ASO primer is downstream and is directed to the most variable region of the rearrangement.

Monitoring by PCR of minimal residual disease (MRD) in leukaemia has become widely used in clinical practice. Typically, decisions are made on whether to continue or change treatment by measuring the number of leukaemic cells (MRD) at the end of induction treatment (approximately one month) and after several cycles of consolidation treatment (approximately 80 days). Typically, a decision may be made to increase the intensity of treatment if the level of MRD at the end of induction is above a defined cut-off level. This cut-off level varies slightly between different group protocols but is typically between $10^{-3}$ (1/1000) and $10^{-4}$ (1/10,000) leukaemic cells/total cells.

The problem which currently exists with this method is nonspecificity which may give rise to false positive results and which, importantly, limits sensitivity of detection and measurement. As a result, it is sometimes not possible to detect, and often not possible to quantify, MRD below a level of $10^{-4}$. This has two consequences:

When MRD is below the limit of detection, quantification is impossible. This is the case for many patients. There is great interest in attempting to identify patients who have responded very well to initial treatment and in whom the intensity of subsequent treatment can be decreased. Such patients would be characterised by having very low levels of MRD e.g. $<10^{-6}$, but, if the limit of detection is 104, they cannot be distinguished from patients with levels between $10^{-4}$ and $10^{-6}$.

Owing to stochastic variation in the assay, the precision of measurement is poor when the level of MRD is close to but still above the limit of detection.

Factors leading to nonspecificity include:

The sequences to which the two primers bind are not unique but are sequences normally present in the genome and the specificity of amplification only arises because of the rearrangement bringing the binding sequences close to each other.

Some degree of homology is present between different members of the V gene family and also between different members of the D gene family. This increases the probability of the upstream primer hybridising to a nonleukaemic rearrangement.

The rearrangements in the population of nonleukaemic lymphocytes are extremely heterogeneous so that there is a real probability that a rearrangement in one or more cells in the normal population will resemble the universal rearrangement in the population of leukaemic cells.

There are many prior art methods which, over the last 18 years, have attempted to minimise the incidence of non-specific amplification. These include:

The performance of a 2-round or 3-round nested PCR using a series of upstream primers targeted to different regions of the rearranged target gene. This eliminates nonspecificity and results in a highly sensitive assay (eg. Morley et al, 2009). However, this approach is more complex and carries the risk of environmental contamination with PCR product.

Replacement of PCR by next-gen sequencing. This procedure can possibly measure MRD down to $10^{-5}$ and, perhaps with extra steps, down to 106. However, the procedure is complex and expensive, particularly if high sensitivity is desired.

Directing the upstream ASO primer to the largest N region and the downstream primer to the germline J sequence, coupled with annealing temperatures of approximately 60° C. (eg. Bruggemann et al, 2004; Pongers-Willemse et al, 1999; Nakao et al, 2000; van der Velden et al, 2002; van der Velden et al, 2004; van der Velden et al, 2007; van der Velden et al, 2009; van der Velden et al, 2014; Verhagen et al, 2000).

A single amplification reaction in which a single primer is directed to one of the N regions or nested amplification reactions in which the first reaction involves a single primer directed to the upstream N region and the second reaction involves a single primer directed to the downstream N region.

The use of primers with Tm up to around 65° C. and/or the use of annealing temperatures of up to 69° C. (Bruggemann et al, 2004; Pongers-Willemse et al, 1999; Nakao et al, 2000; van der Velden et al, 2002; van der Velden et al, 2007; van der Velden et al, 2009; van der Velden et al, 2014; Verhagen et al, 2000).

The use of shortened primers.

Designing the primers to exhibit specific placement characteristics in the context of their positioning on the rearranged gene.

However, these methods have failed to significantly reduce non-specific amplification. Over almost 2 decades and despite conventional wisdom, progressively increasing the annealing temperature from 60° C. up to 69° C. has had only a minor and variable effect on the level of nonspecificity (Bruggemann et al, 2004; Pongers-Willemse et al, 1999; Nakao et al, 2000; van der Velden et al, 2002; van der Velden et al, 2007; van der Velden et al, 2009; van der Velden et al, 2014; Verhagen et al, 2000). Owing to this, routine optimisation of annealing temperature, increasing from the recommended value of 60° C. has failed to produce the desired effect and the use of a single upstream ASO primer designed according to the various prior art placement recommendations in fact leads to the frequent observation of non-specific amplification. Non-specific amplification has been accepted to such an extent that the criteria for interpreting an MRD result recommend relating that result to the level of non-specificity that has been observed (van der Velden et al, 2007).

Accordingly, there is an ongoing need to develop improved amplification methods which are simple, yet exhibit improved sensitivity by virtue of a reduction in the level of non-specific amplification in the context of the detection of rearranged Ig and TCR genes, such as in the context of MRD.

In work leading up to the present invention, a highly sensitive one-round PCR has been developed based on the use of a primer with a Tm of at least 67° C. and/or an annealing temperature of at least 70° C. The reduction in non-specific amplification in reactions which are designed to incorporate these conditions is so significant, and unexpectedly non-linear in terms of its effect, as to provide a reproducible means of enabling quantification of MRD in samples obtained during treatment of patients with acute lymphoblastic leukaemia or chronic lymphocytic leukaemia, this having not been achievable to date. This is both unexpected and entirely counterintuitive when considered in light of the very minor improvements which have been achieved to date in terms of the extensive combinations of progressively higher annealing temperature and primer Tm which have been tested. That there in fact existed a critical temperature beyond which a dramatic improvement in specificity is achievable but which had not been envisaged by the skilled person due to the absence of any significant improvement over a progressive 10° C. temperature increase beyond the typical 59° C./60° C. annealing temperature of PCR reactions was unforeseen. These improvements are maintained even as the annealing temperature is increased well beyond 70° C. Still further, it has been determined that these outcomes are also achievable if the primers are designed to exhibit a Tm at least 67° C.

Finally, the inventors have determined that the use of a primer designed to hybridise to at least two N regions of a rearranged Ig or TCR still further significantly reduces the non-specificity of the PCR reaction.

The development of this method obviates the need to perform more complex multiplex or nested PCR reactions or to otherwise use highly expensive next-gen sequencing. The development of the present method has now enabled the improved detection and/or monitoring of clonal populations of lymphoid cells which are characterised by a specific Ig or TCR gene recombination, such as neoplastic populations of T cells or B cells. There is also provided means of diagnosing and/or monitoring disease conditions which may be characterised by the expansion of such clonal populations of cells.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The present invention is not to be limited in scope by the specific embodiments described herein, which are intended for the purposes of exemplification only. Functionally-equivalent products, compositions and methods are clearly within the scope of the invention, as described herein.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

The subject specification contains nucleotide sequence information prepared using the programme PatentIn Version 3.1, presented herein after the bibliography. Each nucleotide sequence is identified in the sequence listing by the numeric indicator <210> followed by the sequence identifier (eg. <210>1, <210>2, etc). The length, type of sequence (DNA, etc) and source organism for each nucleotide sequence are indicated by information provided in the numeric indicator fields <211>, <212> and <213>, respectively. Nucleotide sequences referred to in the specification are identified by the indicator SEQ ID NO: followed by the sequence identifier (eg. SEQ ID NO:1, SEQ ID NO: 2, etc.). The sequence identifier referred to in the specification correlates to the information provided in numeric indicator field <400> in the sequence listing, which is followed by the sequence identifier (eg. <400>1, <400>2, etc.). That is SEQ ID NO:1 as detailed in the specification correlates to the sequence indicated as <400>1 in the sequence listing.

One aspect of the present invention is directed to a method of amplifying an Ig or TCR nucleic acid region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using at least one primer with a Tm of at least 67° C.

In another aspect of the present invention there is provided a method of amplifying an Ig or TCR nucleic acid region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using an annealing temperature of at least 70° C.

In still another aspect there is provided a method of amplifying an Ig or TCR DNA region which is characterised by the rearrangement of two or more V, D or J gene segments said method comprising contacting a nucleic acid sample of interest with forward and reverse primers directed to said rearranged Ig or TCR nucleic acid region and amplifying said DNA sample using (i) at least one primer with a Tm of at least 67° C. and/or (ii) an annealing temperature of at least 70° C.

In one aspect, said at least one primer is the ASO primer.

In another aspect, said method comprises using both a primer with a Tm of at least 67° C. and an annealing temperature of at least 70° C.

In yet another aspect, the subject primer has a Tm of 67-80° C., in another embodiment a Tm of 68-76° C., and in yet another embodiment a Tm of 69-74° C.

In still another aspect, said annealing temperature is 70° C., 71° C., 72° C., 73° C., 74° C., 75° C., 76° C., 77° C., 78° C., 79° C., 80° C., 81° C., 82° C. or 83° C.

In yet another aspect, there is therefore provided a method of amplifying an Ig or TCR nucleic acid region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using (i) at least one primer with a Tm of 67° C.-80° C. and/or (ii) an annealing temperature of 70° C. to 83° C.

In a further aspect there is provided a method of amplifying an Ig or TCR nucleic acid region which is characterised by the rearrangement of the V, D and J gene segments said method comprising contacting a nucleic acid sample of interest with forward and reverse primers directed to said rearranged V, D and J gene segments wherein at least one of said primers comprises hybridisation subregions directed to at least two N gene segments of the rearranged V, D and J gene segments and amplifying said nucleic acid sample using (i) at least one primer with a Tm of least 67° C.; and/or (ii) an annealing temperature of at least 70° C.

In still yet another aspect there is provided a method of amplifying an Ig or TCR nucleic acid region which is characterised by the rearrangement of the V, D and J gene segments said method comprising contacting a nucleic acid sample of interest with forward and reverse primers directed to said rearranged V, D and J gene segments wherein at least one of said primers hybridises to the $N_1DN_2$ gene segments of the rearranged V, D and J gene segments and amplifying said nucleic acid sample using (i) at least one primer with a Tm of at least 67° C.; and/or (ii) an annealing temperature of at least 70° C.

Another aspect of the present invention provides a method of detecting and/or monitoring a clonal population of cells in a mammal, which clonal cells are characterised by an Ig or TCR nucleic acid region which is characterised by the rearrangement of two or more V, D or J gene segments, said method comprising:

(i) contacting the DNA material of a biological sample derived from a mammal with the forward and reverse primers as hereinbefore defined for a time and under conditions sufficient to facilitate interaction of said primers with said target nucleic acid molecule;
(ii) amplifying said nucleic acid target; and
(iii) detecting said amplified product.

In accordance with the preceding aspects of the present invention, in one embodiment, said clonal cells are a population of clonal lymphoid cells.

In another embodiment at least one of said primers comprises hybridisation subregions directed to at least two N gene segments of the rearranged V, D and J gene segments In still another embodiment, said N gene segments are the $N_1$ and $N_2$ gene segments.

In a further embodiment, said at least one primer hybridises to the rearranged N regions of the $N_1DN_2$ gene segments.

In one embodiment, said nucleic acid is DNA.

In a further embodiment, said primer which hybridises to the $N_1DN_2$ gene segments of the rearranged V, D and J gene segments is the forward primer.

In a further embodiment said at least one primer is the ASO primer.

In still a further embodiment said primer has a Tm of 67° C. to 80° C.

In yet still another embodiment said primer has a Tm of 68-76° C.,

In a further embodiment said primer has a Tm of 69-73° C.

In another embodiment, said annealing temperature is 70° C., 71° C., 72° C.,

73° C., 74° C., 75° C., 76° C., 77° C., 78° C., 79° C., 80° C., 81° C., 82° C. or 83° C.

In still another embodiment, said annealing temperature is 70° C. to 83° C.

In yet another embodiment, said annealing temperature is 71° C. to 80° C.

In a further embodiment, said annealing temperature is 70° C. to 77° C.

In still another embodiment, said annealing temperature is 71° C. to 77° C.

In yet another embodiment, said annealing temperature is 72° C. to 75° C.

In another embodiment, said method comprises using both a primer with a Tm of at least 67° C. and an annealing temperature of at least 70° C.

In a further embodiment where said at least one primer has a Tm of 69° C. to 76° C., said annealing temperature is 70° C. to 78° C.

In still another further embodiment where said at least one primer has a Tm of 69° C. to 76° C., said annealing temperature is 72° C. to 75° C.

In yet another embodiment, where the ASO primer has a Tm of 69° C. to 72° C., said annealing temperature is 72° C.

In still yet another embodiment, where the ASO primer Tm is 72° C. or higher, said annealing temperature is 75° C.

In yet another aspect, said condition is a neoplasia, preferably a lymphoid neoplasia.

In another aspect, the method of the present invention is used to detect minimum residual disease in the context of lymphoid leukaemias.

Yet another aspect of the present invention is directed to an isolated primer as hereinbefore described.

BRIEF DESCRIPTION OF THE DRAWINGS

FIG. 1 provides a tabulated representation of testing function and non-specificity of primers over a range of annealing temperatures. Three primers were tested and their sequences and Tm estimates are shown. In the first row, DO refers to 2 wells each containing 400 μg of leukaemic DNA and Pbl refers to 2 wells each containing 500 ng of non-leukaemic DNA. In the second row, the annealing temperatures are shown. In the third row, the mean Ct values are shown. NA indicates no amplification. Single1 and single2 amplify well and produce no nonspecificity at all annealing temperatures. Single3 shows suboptimal amplification at an annealing temperature of 75 and one well showing nonspecific amplification at an annealing temperature of 69.4.

DETAILED DESCRIPTION OF THE INVENTION

Figure 2:
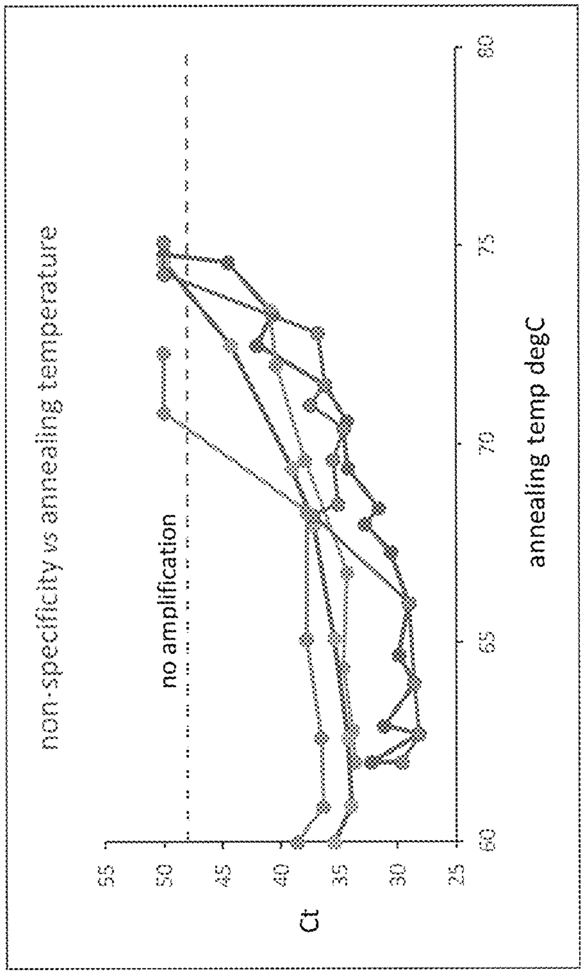
FIG. 2 is a graphical representation of non-specificity vs annealing temperature. PCR was performed using 2 μg non-leukaemic DNA and primer pairs from 5 patients. These primers were chosen for study as they showed some non-specificity at lower temperatures. The amount of non-specificity is inversely proportional to the Ct value. In each case the amount of non-specificity remained approximately the same until the annealing temperature increased above 70° C. It then progressively decreased and eventually could not be detected with 4 of the primer pairs.
Figure 3:
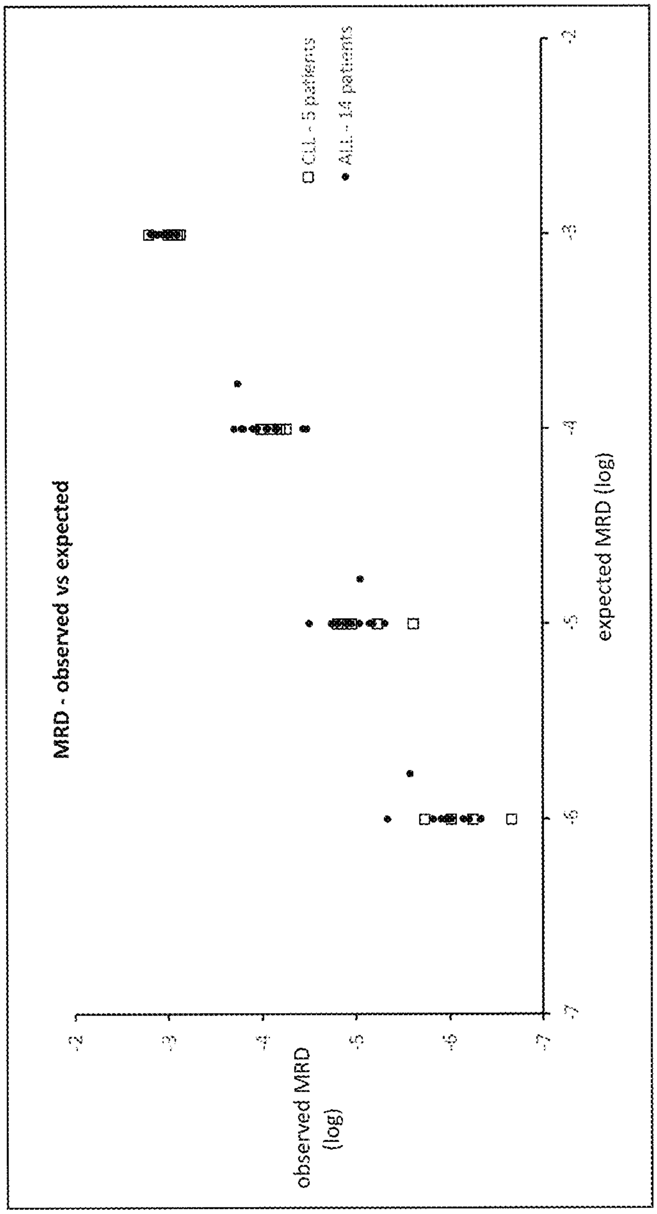
FIG. 3 is a graphical representation of the observed MRD values versus expected MRD values. Leukaemic DNA and non-leukaemic DNA were mixed in various known proportions to provide artificial samples containing a range of levels of MRD. Thirty µg of DNA from each sample were assayed and the levels of MRD observed are related in the Figure to the expected value. Note that with assay of this amount of DNA the limit of detection of MRD is below $10^{-6}$. ALL refers to DNA from patients with acute lymphoblastic leukaemia, CLL refers to DNA from patients with chronic lymphocytic leukaemia.
Figure 4:
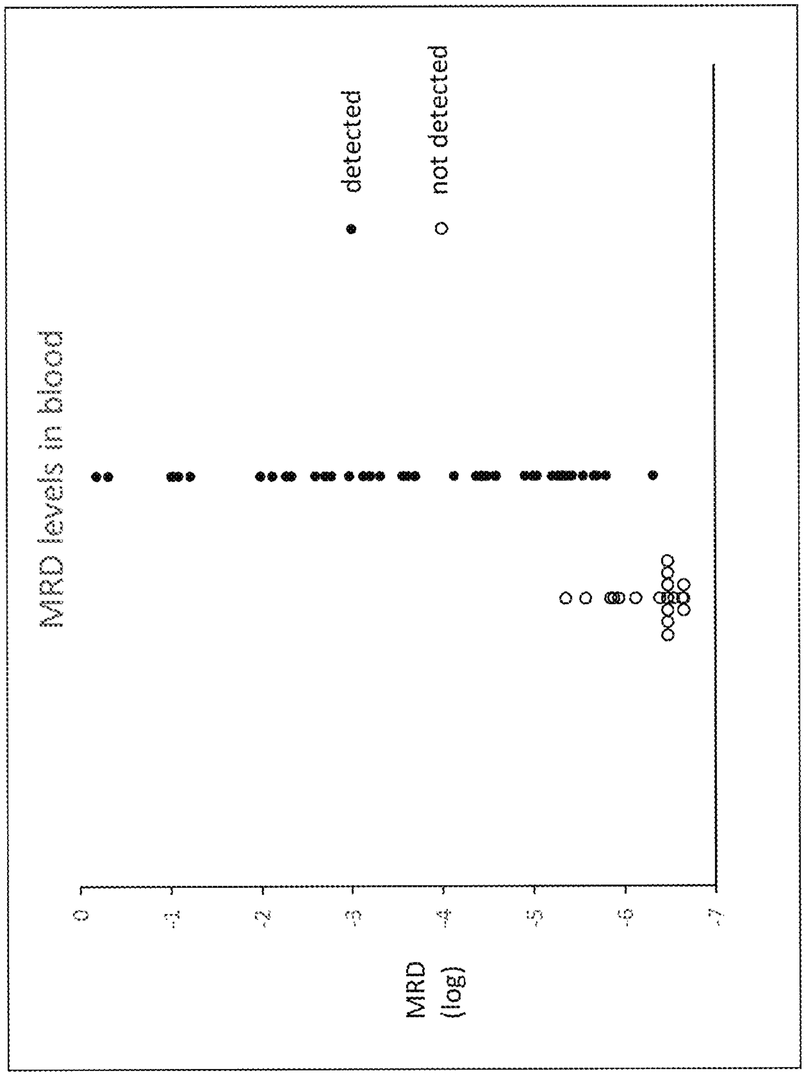
FIG. 4 is a graphical representation of the levels of MRD in samples of blood from patients with acute lymphoblastic leukaemia. Levels below $10^{-6}$ were detected and measured. Samples in which MRD was not detected are also shown and the level of MRD was less than the value indicated. The different values shown for these negative samples reflect the different amounts of sample DNA which were available for assay.

The present invention is predicated, in part, on the development of a simple yet highly sensitive amplification method for detecting a clonal population of cells characterised by a rearranged Ig or TCR gene. The use of either a primer, in particular an ASO primer with a Tm or at least 67° C., and/or an annealing temperature of 70° C. or greater has unexpectedly enabled the development of a highly sensitive single round PCR. Still further, the use of primers which hybridise to at least two N regions of the fully or partially recombined Ig or TCR gene of interest facilitates still further improvements to the sensitivity and specificity of the amplification reaction. The development of this method has now facilitated the detection of specific Ig or TCR gene rearrangements of interest, in particular in the context of detecting or monitoring conditions characterised by the presence of cells, such as clonal populations of cells, expressing a known Ig or TCR gene rearrangement. The methods and primers of the present invention find particular use with respect to the detection of minimal residual disease, which requires high levels of sensitivity and specificity, this currently generally only being achievable via the application of highly complex and expensive molecular techniques.

Accordingly, one aspect of the present invention is directed to a method of amplifying an Ig or TCR nucleic acid region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using at least one primer with a Tm of at least 67° C.

In one embodiment, said at least one primer is the ASO primer.

In another aspect of the present invention there is provided a method of amplifying an Ig or TCR nucleic acid region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using an annealing temperature of at least 70° C.

In another embodiment, said method comprises using both a primer with a Tm of at least 67° C. and an annealing temperature of at least 70° C.

The effect of nucleotide modifications such as locked nucleic acids or bridged nucleic acids or other modifications also needs to be incorporated into the estimation of Tm.

Reference to an "Ig or TCR nucleic acid region" should be understood as a reference to any region of Ig or TCR DNA or RNA which is sought to be amplified. Said nucleic acid region may correspond to a partially rearranged gene or a fully rearranged gene.

Reference to a "nucleic acid" or "nucleotide" should be understood as a reference to both deoxyribonucleic acid or nucleotides and ribonucleic acid or nucleotides or derivatives or analogues thereof. In this regard, it should be understood to encompass phosphate esters of ribonucleotides and/or deoxyribonucleotides, including DNA (cDNA or genomic DNA), RNA or mRNA among others. The nucleic acid molecules of the present invention may be of any origin including naturally occurring (such as would be derived from a biological sample), recombinantly produced or synthetically produced. The nucleic acid may also be a non-standard nucleotide such as inosine.

Reference to "derivatives" should be understood to include reference to fragments, parts, portions, homologs and mimetics of said nucleic acid molecules from natural, synthetic or recombinant sources. "Functional derivatives" should be understood as derivatives which exhibit any one or more of the functional activities of nucleotides or nucleic acid molecules. The derivatives of said nucleotides or nucleic acid sequences include fragments having particular regions of the nucleotide or nucleic acid molecule fused to other proteinaceous or non-proteinaceous molecules. "Analogs" contemplated herein include, but are not limited to, modifications to the nucleotide or nucleic acid molecule such as modifications to its chemical makeup or overall conformation. This includes, for example, modification to the manner in which nucleotides or nucleic acid molecules interact with other nucleotides or nucleic acid molecules such as at the level of backbone formation or complementary base pair hybridisation. The biotinylation of a nucleotide or nucleic acid molecules is an example of a "functional derivative" as herein defined. Derivatives of nucleic acid molecules may be derived from single or multiple nucleotide substitutions, deletions and/or additions. The term "functional derivatives" should also be understood to encompass nucleotides or nucleic acid exhibiting any one or more of the functional activities of a nucleotide or nucleic acid sequence, such as for example, products obtained following natural product screening.

The subject "nucleic acid" region may be DNA or RNA or derivative or analogue thereof. Since the region of interest is a DNA sequence which encodes a proteinaceous molecule it may take the form of genomic DNA, cDNA which has been generated from a mRNA transcript, or DNA generated by nucleic acid amplification. If the subject method is directed to detecting a region of RNA, it would be appreciated that it will first be necessary to reverse transcribe the RNA to DNA, such as using RT-PCR. The subject RNA may be any form of RNA, such as mRNA, primary RNA transcript, ribosomal RNA, transfer RNA, micro RNA or the like. Preferably, said nucleic acid region of interest is a DNA region of interest. To this end, said DNA includes DNA generated by reverse transcription from RNA which is ultimately the subject of analysis, and DNA generated by a nucleic acid amplification method such as PCR.

The nucleic acid region which is the subject of amplification is an Ig or TCR nucleic acid region which has undergone the rearrangement of two or more of the V, D or J gene segments. Accordingly, the subject nucleic acid region of interest may correspond to either a partially or fully rearranged gene. As discussed in more detail hereafter, Ig and TCR rearrangement occurs as a series of sequential rearrangements which result in a fully rearranged variable region which is, in the last step, rearranged to join a constant region gene. The method of the present invention may be amplifying all or part of a partially rearranged gene, depending on the point at which the clonal lymphoid cell may have ceased differentiation.

In one embodiment, said target nucleic acid region is DNA.

According to this embodiment, there is provided a method of amplifying an Ig or TCR DNA region which is characterised by the rearrangement of two or more V, D or J gene segments said method comprising contacting a nucleic acid sample of interest with forward and reverse primers directed to said rearranged Ig or TCR nucleic acid region and amplifying said DNA sample using (i) at least one primer with a Tm of at least 67° C. and/or (ii) an annealing temperature of at least 70° C.

In another embodiment, said at least one primer is the ASO primer.

In still another embodiment, said method comprises using both a primer with a Tm of at least 67° C. and an annealing temperature of at least 70° C.

The method of the present invention is effected by contacting the nucleic acid sample to be tested with forward and reverse primers. Reference to a "primer" or an "oligonucleotide primer" should be understood as a reference to any molecule comprising a sequence of nucleotides, or functional derivatives or analogues thereof, the function of which includes hybridisation to a region of a nucleic acid molecule of interest. The primer may contain one or more locked nucleic acids. It should also be understood that the primer may comprise non-nucleic acid components. For example, the primer may also comprise a non-nucleic acid tag such as a fluorescent or enzymatic tag or some other non-nucleic acid component which facilitates the use of the molecule as a probe or which otherwise facilitates its detection or immobilisation. The primer may also comprise additional nucleic acid components, such as an oligonucleotide tag. In another example, the primer may be a protein nucleic acid which comprises a peptide backbone exhibiting nucleic acid side chains. Preferably, said oligonucleotide primer is a DNA primer. The primers of the present invention are "directed to" a rearranged Ig or TCR nucleic acid. By "directed to" is meant that the primers are designed to hybridise, either partially or in its entirety, to the rearranged Ig or TCR nucleic acid region which is sought to be amplified.

Without limiting the present invention to any one theory or mode of action, V(D)J recombination in organisms with an adaptive immune system is an example of a type of site-specific genetic recombination that helps immune cells rapidly diversify to recognise and adapt to new pathogens. Each lymphoid cell undergoes somatic recombination of its germ line variable region gene segments (either V and J, D and J or V, D and J segments) depending on the particular gene segments rearranged in order to generate a total antigen diversity of approximately $10^{16}$ distinct variable region structures. In any given lymphoid cell, such as a T cell or B cell, at least two distinct variable region gene segment rearrangements are likely to occur due to the rearrangement of two or more of the two chains comprising the TCR or immunoglobulin molecule, specifically, the α, β, γ or δ chains of the TCR and/or the heavy and light chains of the immunoglobulin molecule. In addition to rearrangements of the VJ, DJ or VDJ segment of any given immunoglobulin or TCR gene, nucleotides are randomly removed and/or inserted at the junction between the segments. This leads to the generation of enormous diversity.

The loci for these gene segments are widely separated in the germline but recombination during lymphoid development results in apposition of a V, (D) and J gene, with the junctions between these genes being characterised by small regions of insertion and deletion of nucleotides. This process occurs randomly so that each normal lymphocyte comes to bear a unique V(D)J rearrangement. Since a lymphoid cancer, such as acute lymphoblastic leukaemia, chronic lymphocytic leukaemia, lymphoma or myeloma, occurs as the result of neoplastic change in a single normal cell, all of the cancer cells will, at least originally, bear the junctional V(D)J rearrangement originally present in the founder cell. Subclones may arise during expansion of the neoplastic population and further V(D)J rearrangements may occur in them.

Reference to a "gene segment" should be understood as a reference to the V, D and J regions of the immunoglobulin and T cell receptor genes. The V, D and J gene segments are clustered into families. For example, there are 52 different functional V gene segments for the κ immunoglobulin light chain and 5 J gene segments. For the immunoglobulin heavy chain, there are 55 functional V gene segments, 23 functional D gene segments and 6 J gene segments. Across the totality of the immunoglobulin and T cell receptor V, D and J gene segment families, there are a large number of individual gene segments, thereby enabling enormous diversity in terms of the unique combination of V(D)J rearrangements which can be effected. For the sake of clarity, the rearranged immunoglobulin or T cell receptor [V(D)J] variable nucleic acid region will be referred to herein as a "gene" and the individual V, D or J nucleic acid regions will be referred to as "gene segments". Accordingly, the terminology "gene segment" is not exclusively a reference to a segment of a gene. Rather, in the context of Ig and TCR gene rearrangement, it is a reference to a gene in its own right with these gene segments being clustered into families. A "rearranged" immunoglobulin or T cell receptor variable region gene should be understood herein as a gene in which two or more of one V segment, one J segment and one D segment (if a D segment is incorporated into the particular rearranged variable gene in issue) have been spliced together to form a single rearranged "gene". In fact, this rearranged "gene" is actually a stretch of genomic DNA comprising one V gene segment, one J gene segment and one D gene segment which have been spliced together. It is therefore sometimes also referred to as a "gene region" (although not in the context of this specification) since it is actually made up of 2 or 3 distinct V, D or J genes (herein referred to as gene segments) which have been spliced together. The individual "gene segments" of the rearranged immunoglobulin or T cell receptor gene are therefore defined as the individual V, D and J genes. These genes are discussed in detail on the IMGT database. The term "gene" will be used herein to refer to the rearranged immunoglobulin or T cell receptor variable gene. The term "gene segment" will be used herein to refer to the V, D, J and framework 3 regions. However, it should be noted that there is significant inconsistency in the use of "gene"/"gene segment" language in terms of immunoglobulin and T cell receptor rearrangement. For example, the IMGT refers to individual V, D and J "genes", while some scientific publication refers to these as "gene segments". Some sources refer to the rearranged variable immunoglobulin or T cell receptor as a "gene region" while others refer to it as a "gene". The nomenclature which is used in this specification is as defined earlier.

Still without limiting the present invention to any one theory or mode of action, the nature of genetic recombination events is such that a junction between the recombined genes or gene segments (as defined herein) may be characterised by the deletion and insertion of random nucleotides resulting in the formation of "N regions". These N regions are also unique and are therefore useful targets in the context of the design of the primers of the present invention. In this regard, in order to simplify the discussion in this document in relation to subregions of the primers of the present invention relative to the genes/gene segments to which they bind, these N regions may alternatively be referred to as "gene segments" in the context of the present invention, despite the fact that they do not exist in the chromosome as a discrete gene segment and are generated only at the time of rearrangement due to the insertion and deletion of nucleotides at the site of recombination. The election to refer to these as either N gene segments or N regions is made purely on the basis of simplifying the language of any given section of this document in order to assist with clarity. Accordingly, in the context of V(D)J rearrangement in particular, the gene segments which may be the subject of analysis are the individual V, $N_1$, D, $N_2$ and J regions, as well as the framework 3 gene segment. In this context, the N gene segment between the V and D gene segments is termed $N_1$ and the N gene segment between the D and J gene segments is termed $N_2$. However, it should also be understood that N regions (or "gene segments") may occur within a V, D or J gene segment. Without limiting the present invention to any one theory of mode of action, this is most commonly observed in the context of the D gene segment which, during its rearrangement with the J gene segment can undergo the formation of one or more N regions within the D gene segment. Accordingly, although a fully rearranged VDJ region will generally always include $N_1$ and $N_2$ gene segments, it may also include additional N regions, such as within the V, D or J gene segments or, even, at the junction of the rearranged J gene segment and the constant gene, this final rearrangement usually occurring after the conclusion of the VDJ rearrangement.

Reference to "forward primer" (or "upstream primer" or "ASO primer") should be understood as a reference to a primer which amplifies the target nucleic acid (eg. DNA) in the nucleic acid (eg. DNA) sample of interest by hybridising to the antisense strand of the target DNA and 5' to the other primer.

Reference to "reverse primer" (or "downstream primer") should be understood as a reference to a primer which amplifies the target nucleic acid (eg. DNA) in the nucleic acid (eg. DNA) sample of interest and in the PCR by hybridising to the sense strand of the target nucleic acid (eg. DNA) or 3' to the other primer.

The means to design and synthesise primers suitable for use in the present invention would be well known to those of skill in the art. As detailed hereinbefore, the V, D and J gene segment families have been fully identified and sequenced. Accordingly, the design of primers to amplify specific segments or combinations of rearranged segments is well within the skill of the person in the art. Nevertheless, substantial exemplification is also provided in Example 2 in relation to the synthesis and testing of primers which exhibit the Tm values hereby used.

In relation to Tm, and as would be understood by the skilled person, this is a reference to the primer melting temperature and the temperature at which the primer is 50% hybridised to its exact complement. Without limiting the present invention to any one theory or mode of action, hybridisation of a primer to its complement is impacted upon by a number of factors including the length and sequence of the primer oligonucleotide, the presence of nucleotide modifications, the concentrations of the oligonucleotide and its complement, the concentration of various salts, particularly magnesium, and the presence of various chemicals, such as formamide or dimethylsufoxide, which affect hybridisation. In practice, the Tm of a primer is usually estimated or predicted using a software program rather than being actually measured under the conditions of its use. In one embodiment of the present invention, the Tm value is an estimated or predicted value rather than an actual measured value. For example, the primer Tm values may be estimated using the OligoAnalyzer 3.1 program provided by IDT. Further exemplification is provided in Examples 1 and 2. However, the design and synthesis of primers which are required to meet certain specific Tm parameters would be well known to those skilled in the art.

Without limiting the present invention in any way, in terms of the embodiments of the present invention which are exemplified herein, the Tm value is an estimated or predicted value rather than an actual measured value. For the present invention, the primer Tm values have been estimated using the OligoAnalyzer 3.1 program provided by IDT using a magnesium concentration of 5 mM and concentration of each nucleotide triphosphate of 300 μM. The settings, assumptions and limitations of the OligoAnalyzer 3.1 program as shown on the website are documented in Example 1. The skilled person would be aware that use of different salt or oligonucleotide concentrations, or various oligonucleotide modifications, or calculation using a program different from OligoAnalyzer 3.1, might give a predicted Tm value different from that given by the OligoAnalyzer 3.1 program. However for use in the present invention, the predicted Tm can be converted back to that provided by the OligoAnalyzer 3.1 program (or a program providing similar results) using a magnesium concentration of 5 mM and concentration of each nucleotide triphosphate of 300 μM. The effect of nucleotide modifications such as locked nucleic acids or bridged nucleic acids or other modifications are also incorporated into the estimation of Tm.

As detailed hereinbefore, it has been determined that by performing the amplification reaction either using at least one primer, preferably the ASO primer, with a Tm of 67° C. or greater and/or an annealing temperature of at least 70° C., an unexpectedly significant improvement in amplification sensitivity can be achieved, this having been entirely counterintuitive based on prior art investigations which demonstrated a very minor decrease in non-specificity as the annealing temperature was increased from the typical 60° C. up to 69° C., the consequential minor improvement being inadequate for clinical purposes, such as the measurement of MRD. In this regard, reference to "annealing temperature" should be understood as a reference to the temperature of the phase of amplification during which hybridisation of the primers to the target nucleic acid region (template) occurs.

Accordingly, in one embodiment, the subject primer has a Tm of 67-80° C., in another embodiment a Tm of 68-76° C., and in yet another embodiment a Tm of 69-74° C.

In another embodiment, said annealing temperature is 70° C., 71° C., 72° C., 73° C., 74° C., 75° C., 76° C., 77° C., 78° C., 79° C., 80° C., 81° C., 82° C. or 83° C.

According to this embodiment, there is therefore provided a method of amplifying an Ig or TCR nucleic acid region which is characterised by the rearrangement of two or more V, D or J gene segments said method comprising contacting a nucleic acid sample of interest with forward and reverse primers directed to said rearranged Ig or TCR nucleic acid region and amplifying said nucleic acid sample using (i) at least one primer with a Tm of 67° C.-80° C. and/or (ii) an annealing temperature of 70° C. to 83° C.

In one embodiment, said at least one primer has a Tm of 68° C.-76° C.

In another embodiment, said at least one primer has a Tm of 69° C.-73° C.

In a further embodiment, said at least one primer is the ASO primer.

In still another embodiment, said annealing temperature is 71° C. to 80° C.

In a further embodiment, said annealing temperature is 70° C. to 77° C.

In still another further embodiment, said annealing temperature is 71° C. to 77° C.

In yet another embodiment, said annealing temperature is 72° C. to 75° C.

It would be appreciated by the skilled person that one may optimise the annealing temperature to the Tm of the primer which is selected for use, such as the ASO primer. It would be appreciated that means for optimising Tm and annealing temperature relative to one another are also well within the abilities of the skilled person. In this regard since the forward and reverse primers may exhibit different hybridization specificities, for example, the ASO primer relative to the other primer, which will usually be the downstream (reverse) primer, the Tm of the two primers may vary somewhat. In this case, the Tm optimisation is preferably calculated relative to the ASO primer, which is usually the forward primer. The reverse primer, which may therefore be utilized together with a range of different ASO forward primers should be designed to work with a range of annealing temperatures. For example, a Tm of 69° C. may be suitable for a range of annealing temperatures, such as annealing temperatures in the range of 70° C. to 73° C. Although well known to the skilled person, teaching in relation to selecting the appropriate annealing temperature for a primer with a given Tm is provided in Example 2.

In yet another embodiment, where said ASO primer Tm is 69° C. to 72° C., said annealing temperature is 72° C.

In still another embodiment, where said ASO primer Tm is 72° C. or higher, said annealing temperature is 75° C.

As detailed hereinbefore, the forward primer is usually the ASO primer, being directed to the most variable region of the IgH or TCR rearrangement, and the reverse primer is directed to a down stream gene segment of the IgH or TCR gene. Since the improved sensitivity afforded by the present invention results from reduced non-specificity, it is advantageous to design the primers to the down stream gene segment to minimise non-specificity. Accordingly, in another embodiment, the primer directed to the downstream gene segment has a Tm of 67° C. or greater and/or is used at an annealing temperature of 70° C. or greater.

In a further embodiment, the skilled person may seek to design and sysnthesise the primer to further enable optimal hybridisation, such as by inserting one or more A and/or T nucleotides at the 3' end of the primer. For example, one may include at least one A or T primer at the 3' of either or both of the forward or reverse primers. In another example, said A or T nucleotide is included at the 3' end of the reverse primer alone, at the 3' end of the J primer or in any of the J primers which are disclosed in Table 1.

As detailed hereinbefore, still further sensitivity can be achieved if the primers are designed to hybridise to at least two N regions (also alternatively termed "gene segments" in this specification) of the rearranged Ig or TCR gene. It would be appreciated by the person of skill in the art that not only will a complete Ig heavy chain gene rearrangement or a complete TCR β chain gene rearrangement, which both comprise a VDJ rearrangement, include two N regions ($N_1$ and $N_2$), but a partial rearrangement may also comprise two or more N regions if one or more of the V, D or J gene segments exhibit internal N regions which form during the rearrangement process. The Ig light chain and the TCR a chain, for example, comprise only a VJ rearrangement, while a partial DJ rearrangement of the IgH chain and TCR B chain occurs prior to the completion of the rearrangement of a V gene segment with the DJ recombination. Accordingly, a VDJ rearrangement will generate two N regions (occasionally more than two if N regions within the V, D or J gene segments are generated), these being configured as $VN_1DN_2J$, while the Ig light chain, TCR a chain or the transient partial rearrangements may generate only one N region, such as VNJ or DNJ. However, if the partially rearranged V, D or J gene segments have acquired N regions within the V, D or J gene segment, the method of this embodiment of the invention can be utilised since at least two N regions are present. In terms of rearrangements which only involve a VJ or DJ rearrangement and which comprise only one N region, the improved sensitivity of the present invention is achieved based only on the application of the annealing temperature and/or Tm described herein. This may apply, for example, to genetic loci such as IGκ and TCRγ which do not contain D genes and the rearrangement involves only the V and J genes. This may also apply to rearrangements of the IGH or TCRβ genes where there is only a "partial" rearrangement which may have a VJ or DJ structure and only one N region.

Accordingly, in yet another embodiment there is provided a method of amplifying an Ig or TCR nucleic acid region which is characterised by the rearrangement of the V, D and J gene segments said method comprising contacting a nucleic acid sample of interest with forward and reverse primers directed to said rearranged V, D and J gene segments wherein at least one of said primers comprises hybridisation subregions directed to at least two N gene segments of the rearranged V, D and J gene segments and amplifying said nucleic acid sample using (i) at least one primer with a Tm of least 67° C.; and/or (ii) an annealing temperature of at least 70° C.

In one embodiment, said N gene segments are the $N_1$ and $N_2$ gene segments.

In another embodiment, said at least one primer hybridises to the rearranged N regions of the $N_1DN_2$ gene segments.

In another embodiment, said nucleic acid is DNA.

In a further embodiment said at least one primer is the ASO primer.

In still a further embodiment said primer has a Tm of 67° C. to 80° C.

In yet still another embodiment said primer has a Tm of 68-76° C.,

In a further embodiment said primer has a Tm of 69-73° C.

In another embodiment, said annealing temperature is 70° C., 71° C., 72° C., 73° C., 74° C., 75° C., 76° C., 77° C., 78° C., 79° C., 80° C., 81° C., 82° C. or 83° C.

In still another embodiment, said annealing temperature is 70° C. to 83° C.

In yet another embodiment, said annealing temperature is 71° C. to 80° C.

In a further embodiment, said annealing temperature is 70° C. to 77° C.

In still another embodiment, said annealing temperature is 71° C. to 77° C.

In yet another embodiment, said annealing temperature is 72° C. to 75° C.

In yet still another embodiment, said method comprises using both a primer with a Tm of at least 67° C. and an annealing temperature of at least 70° C.

In a further embodiment where said at least one primer has a Tm of 69° C. to 76° C., said annealing temperature is 70° C. to 78° C.

In still another further embodiment where said at least one primer has a Tm of 69° C. to 76° C., said annealing temperature is 72° C. to 75° C.

In yet another embodiment, where the ASO primer has a Tm of 69° C. to 72° C., said annealing temperature is 72° C.

In still yet another embodiment, where the ASO primer Tm is 72° C. or higher, said annealing temperature is 75° C.

In still another embodiment, the primer directed to the downstream gene segment has a Tm of at least 67° C. and/or is used at an annealing temperature of at least 70° C.

In another embodiment, said primer directed to the downstream gene segment is directed to the J segment.

As detailed hereinbefore, in the context of this embodiment of the present invention, the primers achieve their improved sensitivity by virtue of the design of the primers such that they hybridise to at least two N gene segments, such as the $N_1$ gene segment 5' to the D gene segment, the $N_2$ gene segment 3' to the D gene segment of a fully rearranged VDJ gene or the N regions (gene segments) which may be formed within a rearranged V, D or J gene segment. In this regard, it should be understood that the improved sensitivity of this embodiment of the present invention is achieved provided that at least one of the forward or reverse primers hybridises to at least two N gene segments. In a preferred embodiment, it is the forward (ASO) primer which hybridises to the two N gene segments. In this embodiment, the reverse primer may hybridise to a downstream gene segment, such as the J gene segment and need not even necessarily be patient specific. In another embodiment, it is the reverse primer which hybridises to the at least two N gene segments.

The design of the primers of the present invention is such that in order to hybridise across two N gene segments, the primers must hybridise across at least three consecutive gene segments of the recombined gene of interest wherein the 5' and 3' gene segments of these three consecutive gene segments are the N regions. Accordingly, the primer is structured such that it comprises three subregions which are each designed to hybridise to one of the three consecutive gene segments of the recombined gene of interest, two of which are N gene segments. By "consecutive" is meant that the three gene segments have been recombined such that they are directly adjacent to one another, preferably in a linear arrangement. In this regard, it should be understood that each of the three subregions of the primer which hybridise to the three recombined and consecutive gene segments are operably linked to one another to form a single primer.

The primer subregions may be the same or different in terms of length. It should be understood that depending on the length of each of these oligonucleotide subregions and the specific gene segment target to which they are directed, they may exclusively hybridise to all or part of just one gene segment or they may hybridise to all or part of each of a number of gene segments. Conceptually, a primer to a partial rearrangement (DNJ or VNJ) may be designed to hybridise to one of the following rearranged gene segment targets: DN, NJ, DNJ, VN, NJ, VNJ, provided that at least one other N region is found within the relevant V, D or J gene segment, such that the primer is thereby hybridising to two N regions. Similarly, a primer to a complete $VN_1DN_2J$ rearrangement may be designed to hybridise, for example, to one of the following rearranged gene segment targets: $VN_1$, $N_1D$, $VN_1D$, $N_1DN_2$, $VN_1DN_2$, $N_1DN_2J$, $VN_1DN_2J$, $N_2$, $DN_2$, $N_2J$, $DN_2J$, provided that where the primer is directed to only one of $N_1$ or $N_2$ gene segment, the second N region which is targeted is found within one of the relevant V, D or J gene segments, such that the primer is thereby hybridising to two N regions.

As would be appreciated, when the primer is designed to hybridise to two N gene segments the primer will span the full length of the gene segment intervening the two N gene segments. The usual context is a VDJ rearrangement and the intervening gene segment is usually the D gene segment. It would be appreciated by the person of skill in the art that due to the length of the D gene segment, designing a primer which hybridises across the full length of the D gene segment can result in a loss of specificity due to the fact that the subregion of the primer which hybridises to the D gene segment is likely to represent the longest subregion of the primer, since the N gene segments are usually relatively short. The specificity for the N gene segments may therefore be compromised since most of the hybridisation of the primer will be determined by its complementarity to the D gene segment. Since the specific D gene segment of interest is likely to be found in many other VDJ rearrangement combinations, in addition to unrearranged genes, it will therefore be detectable in many different cells other than just the cell of interest. This can result in significant false positive results. To reduce the incidence of this non-specific binding, modifications can be made to the subregion of the primer which hybridises to the D gene segment, in order to reduce its specificity. Methods of achieving this include, but are not limited to:

(i) The introduction of one or more spacers or linkers to the subregion of the primer which is designed to hybridise to the D gene segment (or other gene segment to which specificity is sought to be reduced) to decrease hybridisation of that subregion of the oligonucleotide to the D gene segment.

(ii) Synthesis of the primer such that at a number of nucleotide positions within the subregion of the primer which is designed to hybridise to the gene segment, such as the D gene segment, the addition of a single nucleotide is replaced by the addition of a nucleotide randomly selected from an equimolar mixture of all 4 nucleic acid bases (referred to as an N mixture). This significantly reduces the contribution of hydrogen bonding at these positions to the overall hybridisation of the oligonucleotide primer since with each round of amplification at the substituted position there is only a 1 in 4 probability of appropriate bonding between the template nucleotide and the oligonucleotide nucleotide. The use of a less random N mixture e.g. only A/T, has a lesser effect.

Without limiting the present invention to any one theory or mode of action, it has been determined that modifying with an N mixture either approximately every fourth base or a string of 3-7 adjacent nucleotides of a primer subregion which is directed to a lengthy gene segment can achieve a sufficient reduction in specificity but without the loss of primer functionality. It would be appreciated by the skilled person that although this issue is exemplified by reference to the D gene segment, this issue applies equally to other lengthy gene or gene segment sequences which intervene two N regions.

Accordingly, in still yet another embodiment there is provided a method of amplifying an Ig or TCR nucleic acid region which is characterised by the rearrangement of the V, D and J gene segments said method comprising contacting a nucleic acid sample of interest with forward and reverse primers directed to said rearranged V, D and J gene segments wherein at least one of said primers hybridises to the $N_1DN_2$ gene segments of the rearranged V, D and J gene segments and amplifying said nucleic acid sample using (i) at least one primer with a Tm of at least 67° C.; and/or (ii) an annealing temperature of at least 70° C.

In one embodiment, said nucleic acid is DNA.

In a further embodiment, said primer which hybridises to the $N_1DN_2$ gene segments of the rearranged V, D and J gene segments is the forward primer.

In a further embodiment said at least one primer is the ASO primer.

In yet another further embodiment said forward primer which hybridises to the $N_1DN_2$ gene segments of the rearranged V, D and J gene segments comprises one or more nucleotides which are substituted by an N mixture. In still a further embodiment said primer has a Tm of 67° C. to 80° C.

In yet still another embodiment said primer has a Tm of 68-76° C.,

In a further embodiment said primer has a Tm of 69-73° C.

In another embodiment, said annealing temperature is 70° C., 71° C., 72° C.,

73° C., 74° C., 75° C., 76° C., 77° C., 78° C., 79° C., 80° C., 81° C., 82° C. or 83° C.

In still another embodiment, said annealing temperature is 70° C. to 83° C.

In yet another embodiment, said annealing temperature is 71° C. to 80° C.

In a further embodiment, said annealing temperature is 70° C. to 77° C.

In still another embodiment, said annealing temperature is 71° C. to 77° C.

In yet another embodiment, said annealing temperature is 72° C. to 75° C.

In another embodiment, said method comprises using both a primer with a Tm of at least 67° C. and an annealing temperature of at least 70° C.

In a further embodiment where said at least one primer has a Tm of 69° C. to 76° C., said annealing temperature is 70° C. to 78° C.

In still another further embodiment where said at least one primer has a Tm of 69° C. to 76° C., said annealing temperature is 72° C. to 75° C.

In yet another embodiment, where the ASO primer has a Tm of 69° C. to 72° C., said annealing temperature is 72° C.

In still yet another embodiment, where the ASO primer Tm is 72° C. or higher, said annealing temperature is 75° C.

In still another embodiment, the primer directed to the downstream gene segment has a Tm of at least 67° C. and/or is used at an annealing temperature of at least 70° C.

In another embodiment, said primer directed to the downstream gene segment is directed to the J segment and, optionally, comprises one or more A and/or T nucleotides as its 3' end.

Examples of primers suitable for use in the context of hybridising to the J segment are provided in Table 1, below.

TABLE 1

| name | sequence | Tm | SEQ ID NO |
|---|---|---|---|
| IGH | | | |
| AAMJ1b | ctttgctgagcacctgtccccaagtctgaa | 73.2 | SEQ ID NO: 1 |
| AAMJ2 | aggccggctgcagaccccagata | 74 | SEQ ID NO: 2 |
| AAMJ3c | cccccggacattatctcccagctcca | 72.9 | SEQ ID NO: 3 |
| AAMJ4c | gettatttccccccaaaatgcagcaaaaccat | 73.4 | SEQ ID NO: 4 |
| AAMJ5c | cctccaaaatgcctccaagactctgaccctga | 73.5 | SEQ ID NO: 5 |
| AAMJ6c | aggaaaccccacaggcagtagcagaaaacaa | 73.3 | SEQ ID NO: 6 |
| TCR | | | |
| TCR1.1b | ttccctgtgacggatctgcaaaagaacctga | 72.8 | SEQ ID NO: 7 |
| TCR1.2b | ccctcctagagacccccagccttacctacaa | 73.6 | SEQ ID NO: 8 |
| TCR1.3b | caagttcccagctgtccagccttgacttact | 72.7 | SEQ ID NO: 9 |
| TCR1.4b | ccaggaactccgaccttatgatacactatcccgaaagaa | 72.9 | SEQ ID NO: 10 |
| TCR1.5b | atggccataccaccctgattctgcaacttaccta | 73.3 | SEQ ID NO: 11 |
| TCR1.6b | gagtcaagagtggagcccccatacctgt | 72.4 | SEQ ID NO: 12 |
| TCR2.1b | cacctggagcccccttcttacctagca | 72.6 | SEQ ID NO: 13 |
| TCR2.2b | cggagccccaaccgcctcctt | 73.6 | SEQ ID NO: 14 |
| TCR2.3b | ggagccccgcttaccgagcact | 72.9 | SEQ ID NO: 15 |
| TCR2.4b | ccggcggccccagctt | 71.6 | SEQ ID NO: 16 |

TABLE 1-continued

| name | sequence | Tm | SEQ ID NO |
|---|---|---|---|
| TCR2.5b | gcgctcaccgagcaccagga | 71.8 | SEQ ID NO: 17 |
| TCR2.6b | cgcgaaaactcacccagcacggtca | 73.1 | SEQ ID NO: 18 |
| TCR2.7d | ggaaggtggggagacgcccgaat | 72.6 | SEQ ID NO: 19 |

Facilitating the interaction of the primer of the present invention with the target DNA may be performed by any suitable method. Those methods will be known to those skilled in the art. Methods for achieving primer directed amplification are also very well known to those of skill in the art. In one method, said amplification is polymerase chain reaction, NASBA or strand displacement amplification. Preferably, said amplification is polymerase chain reaction.

Reference to a "sample" should be understood as a reference to either a biological or a non-biological sample. Examples of non-biological samples includes, for example, the nucleic acid products of synthetically produced nucleic acid populations. Reference to a "biological sample" should be understood as a reference to any sample of biological material derived from a mammal or mammalian tissue culture such as, but not limited to, cellular material, blood, mucus, faeces, urine, tissue biopsy specimens or fluid which has been introduced into the body of an animal and subsequently removed (such as, for example, the saline solution extracted from the lung following lung lavage or the solution retrieved from an enema wash). The biological sample which is tested according to the method of the present invention may be tested directly or may require some form of treatment prior to testing. For example, a biopsy sample may require homogenisation prior to testing. Further, to the extent that the biological sample is not in liquid form it may require the addition of a reagent, such as a buffer, to mobilise the sample.

To the extent that the target DNA is present in a biological sample, the biological sample may be directly tested or else all or some of the nucleic acid material present in the biological sample may be isolated prior to testing. It is within the scope of the present invention for the target nucleic acid molecule to be pre-treated prior to testing, for example inactivation of live virus or being run on a gel. It should also be understood that the biological sample may be freshly harvested or it may have been stored (for example by freezing) prior to testing or otherwise treated prior to testing (such as by undergoing culturing).

Reference to "contacting" the sample with the primer should be understood as a reference to facilitating the mixing of the primer with the sample such that interaction (for example, hybridisation) can occur. Means of achieving this objective would be well known to those of skill in the art.

The choice of what type of sample is most suitable for testing in accordance with the method disclosed herein will be dependent on the nature of the situation, such as the nature of the condition being monitored. For example, in a preferred embodiment a neoplastic condition is the subject of analysis. If the neoplastic condition is a lymphoid leukaemia, a blood sample, lymph fluid sample or bone marrow aspirate would likely provide a suitable testing sample. Where the neoplastic condition is a lymphoma, a lymph node biopsy or a blood or marrow sample would likely provide a suitable source of tissue for testing. Consideration would also be required as to whether one is monitoring the original source of the neoplastic cells or whether the presence of metastases or other forms of spreading of the neoplasia from the point of origin is to be monitored. In this regard, it may be desirable to harvest and test a number of different samples from any one mammal. Choosing an appropriate sample for any given detection scenario would fall within the skills of the person of ordinary skill in the art.

The term "mammal" to the extent that it is used herein includes humans, primates, livestock animals (e.g. horses, cattle, sheep, pigs, donkeys), laboratory test animals (e.g. mice, rats, rabbits, guinea pigs), companion animals (eg. dogs, cats) and captive wild animals (eg. kangaroos, deer, foxes). preferably, the mammal is a human or a laboratory test animal. Even more preferably the mammal is a human.

The method of this aspect of the present invention provides a means for both detecting the presence of a target nucleic acid region of interest (such as for diagnostic or monitoring purposes) and, optionally, quantifying and/or isolating that target. Accordingly, one is provided with means of detecting, enriching or purifying a target nucleic acid population of interest for any purpose, such as further analysis of the target.

Another aspect of the present invention provides a method of detecting and/or monitoring a clonal population of cells in a mammal, which clonal cells are characterised by an Ig or TCR nucleic acid region which is characterised by the rearrangement of two or more V, D or J gene segments, said method comprising:

(i) contacting the DNA material of a biological sample derived from a mammal with the forward and reverse primers as hereinbefore defined for a time and under conditions sufficient to facilitate interaction of said primers with said target nucleic acid molecule;
(ii) amplifying said nucleic acid target; and
(iii) detecting said amplified product.

Reference to "cells" should be understood as a reference to all forms of cells from any species and to mutants or variants thereof. Preferably, the cell is a lymphoid cell, although the method of the present invention can be performed on any type of cell which may have undergone a partial or full Ig or TCR rearrangement. Without limiting the present invention to any one theory or mode of action, a cell may constitute an organism (in the case of unicellular organisms) or it may be a subunit of a multicellular organism in which individual cells may be more or less specialised (differentiated) for particular functions. All living organisms are composed of one or more cells. The subject cell may form part of the biological sample which is the subject of testing in a syngeneic, allogeneic or xenogeneic context. A syngeneic context means that the clonal cell population and the biological sample within which that clonal population exists share the same MHC genotype. This will most likely be the case where one is screening for the existence of a neoplasia in an individual, for example. An "allogeneic" context is where the subject clonal population in fact expresses a different MHC to that of the individual from which the biological sample is harvested. This may occur, for example, where one is screening for the proliferation of a transplanted donor cell population (such as an immunocompetent bone marrow transplant) in the context of a condition such as graft versus host disease. A "xenogeneic" context is where the subject clonal cells are of an entirely different species to that of the subject from which the biological sample is derived. This may occur, for example, where a potentially neoplastic donor population is derived from xenogeneic transplant.

"Variants" of the subject cells include, but are not limited to, cells exhibiting some but not all of the morphological or phenotypic features or functional activities of the cell of which it is a variant. "Mutants" includes, but is not limited to, cells which have been naturally or non-naturally modified such as cells which are genetically modified.

By "clonal" is meant that the subject population of cells has derived from a common cellular origin. For example, a population of neoplastic cells is derived from a single cell which has undergone transformation at a particular stage of differentiation. In this regard, a neoplastic cell which undergoes further nuclear rearrangement or mutation to produce a genetically distinct population of neoplastic cells is also a "clonal" population of cells, albeit a distinct clonal population of cells. In another example, a T or B lymphocyte which expands in response to an acute or chronic infection or immune stimulation is also a "clonal" population of cells within the definition provided herewith. In yet another example, the clonal population of cells is a clonal microorganism population, such as a drug resistant clone which has arisen within a larger microorganismal population. Preferably, the subject clonal population of cells is a neoplastic population of cells or a clonal immune cell population.

In one embodiment, said clonal cells are a population of clonal lymphoid cells.

In another embodiment at least one of said primers comprises hybridisation subregions directed to at least two N gene segments of the rearranged V, D and J gene segments In still another embodiment, said N gene segments are the $N_1$ and $N_2$ gene segments.

In a further embodiment, said at least one primer hybridises to the rearranged N regions of the $N_1DN_2$ gene segments.

In one embodiment, said nucleic acid is DNA.

In a further embodiment, said primer which hybridises to the $N_1DN_2$ gene segments of the rearranged V, D and J gene segments is the forward primer.

In a further embodiment said at least one primer is the ASO primer.

In yet another further embodiment said forward primer which hybridises to the $N_1DN_2$ gene segments of the rearranged V, D and J gene segments comprises one or more nucleotides which are substituted by an N mixture.

In still a further embodiment said primer has a Tm of 67° C. to 80° C.

In yet still another embodiment said primer has a Tm of 68-76° C.,

In a further embodiment said primer has a Tm of 69-73° C.

In another embodiment, said annealing temperature is 70° C., 71° C., 72° C.,

73° C., 74° C., 75° C., 76° C., 77° C., 78° C., 79° C., 80° C., 81° C., 82° C. or 83° C.

In still another embodiment, said annealing temperature is 70° C. to 83° C.

In yet another embodiment, said annealing temperature is 71° C. to 80° C.

In a further embodiment, said annealing temperature is 70° C. to 77° C.

In still another embodiment, said annealing temperature is 71° C. to 77° C.

In yet another embodiment, said annealing temperature is 72° C. to 75° C.

In another embodiment, said method comprises using both a primer with a Tm of at least 67° C. and an annealing temperature of at least 70° C.

In a further embodiment where said at least one primer has a Tm of 69° C. to 76° C., said annealing temperature is 70° C. to 78° C.

In still another further embodiment where said at least one primer has a Tm of 69° C. to 76° C., said annealing temperature is 72° C. to 75° C.

In yet another embodiment, where the ASO primer has a Tm of 69° C. to 72° C., said annealing temperature is 72° C.

In still yet another embodiment, where the ASO primer Tm is 72° C. or higher, said annealing temperature is 75° C.

In still another embodiment, the primer directed to the downstream gene segment has a Tm of at least 67° C. and/or is used at an annealing temperature of at least 70° C.

In another embodiment, said primer directed to the downstream gene segment is directed to the J segment and, optionally, comprises at least one A or T nucleotides at its 3' end. It should be understood that reference to "lymphoid cell" is a reference to any cell which has rearranged at least one germ line set of immunoglobulin or TCR variable region gene segments. The immunoglobulin variable region encoding genomic DNA which may be rearranged includes the variable regions associated with the heavy chain or the κ or λ light chain while the TCR chain variable region encoding genomic DNA which may be rearranged include the α, β, γ and δ chains. In this regard, a cell should be understood to fall within the scope of the "lymphoid cell" definition provided the cell has rearranged the variable region encoding DNA of at least one immunoglobulin or TCR gene segment region. It is not necessary that the cell is also transcribing and translating the rearranged DNA. In this regard, "lymphoid cell" includes within its scope, but is in no way limited to, immature T and B cells which have rearranged the TCR or immunoglobulin variable region gene segments but which are not yet expressing the rearranged chain (such as TCR-thymocytes) or which have not yet rearranged both chains of their TCR or immunoglobulin variable region gene segments. This definition further extends to lymphoid-like cells which have undergone at least some TCR or immunoglobulin variable region rearrangement but which cell may not otherwise exhibit all the phenotypic or functional characteristics traditionally associated with a mature T cell or B cell. Accordingly, the method of the present invention can be used to monitor neoplasias of cells including, but not limited to, lymphoid cells at any differentiative stage of development, activated lymphoid cells or non-lymphoid/lymphoid-like cells provided that rearrangement of at least part of one variable region gene region has occurred. It can also be used to monitor the clonal expansion which occurs in response to a specific antigen.

With respect to this aspect of the present invention, reference to "monitoring" should be understood as a reference to testing the subject for the presence or level of the subject clonal population of cells after initial diagnosis of the existence of said population. "Monitoring" includes reference to conducting both isolated one off tests or a series of tests over a period of days, weeks, months or years. The tests may be conducted for any number of reasons including, but not limited to, predicting the likelihood that a mammal which is in remission will relapse, screening for minimal residual disease, monitoring the effectiveness of a treatment protocol, checking the status of a patient who is in remission, monitoring the progress of a condition prior to or subsequently to the application of a treatment regime, in order to assist in reaching a decision with respect to suitable treatment or in order to test new forms of treatment. The method of the present invention is therefore useful as both a clinical tool and a research tool.

It should also be understood that although it is preferable that the rearrangement of at least one variable region gene region has been completed, the method of the present invention is nevertheless applicable to monitoring neoplastic cells which exhibit only partial rearrangement. For example, a B cell which has only undergone the DJ recombination event is a cell which has undergone only partial rearrangement. Complete rearrangement will not be achieved until the DJ recombination segment has further recombined with a V segment. The method of the present invention can therefore be designed to detect the partial or complete variable region rearrangement of one TCR or immunoglobulin chain utilising a reference molecule complementary to this marker sequence or, for example, if greater specificity is required and the neoplastic cell has rearranged the variable region of both TCR or immunoglobulin chains, primer molecules directed to both forms of rearrangement can be utilised.

Reference to a “neoplastic cell” should be understood as a reference to a cell exhibiting abnormal “growth”. The term “growth” should be understood in its broadest sense and includes reference to proliferation. In this regard, an example of abnormal cell growth is the uncontrolled proliferation of a cell. The uncontrolled proliferation of a lymphoid cell may lead to a population of cells which take the form of either a solid tumour or a single cell suspension (such as is observed, for example, in the blood of a leukemic patient). A neoplastic cell may be a benign cell or a malignant cell. In a preferred embodiment, the neoplastic cell is a malignant cell. In this regard, reference to a “neoplastic condition” is a reference to the existence of neoplastic cells in the subject mammal. Although “neoplastic lymphoid condition” includes reference to disease conditions which are characterised by reference to the presence of abnormally high numbers of neoplastic cells such as occurs in leukemias, lymphomas and myelomas, this phrase should also be understood to include reference to the circumstance where the number of neoplastic cells found in a mammal falls below the threshold which is usually regarded as demarcating the shift of a mammal from an evident disease state to a remission state or vice versa (the cell number which is present during remission is often referred to as the “minimal residual disease”). Still further, even where the number of neoplastic cells present in a mammal falls below the threshold detectable by the screening methods utilised prior to the advent of the present invention, the mammal is nevertheless regarded as exhibiting a “neoplastic condition”.

Disease conditions suitable for analysis in this regard are any lymphoid malignancies such as acute lymphoblastic leukaemia, chronic lymphocytic leukaemia, lymphoma and myeloma. Monitoring of minimal residual disease is of importance in all of these conditions one example. Examples of primers used for monitoring acute lymphoblastic leukaemia are shown in Example 3, worksheets for assessing primers and quantifying samples are shown in Examples 4-6.

Preferably, said condition is a neoplasia and even more preferably a lymphoid neoplasia.

In one particular embodiment, the method of the present invention is used to detect minimum residual disease in the context of lymphoid leukaemias.

Yet another aspect of the present invention is directed to an isolated primer as hereinbefore described.

Yet still another aspect of the present invention is directed to a kit for facilitating the identification of an Ig or TCR nucleic acid region which is characterised by the rearrangement of two or more V, D or J gene segments, said kit comprising compartments adapted to contain any one or more of the oligonucleotide primers as hereinbefore defined, reagents useful for facilitating interaction of said primer with the target nucleic acid molecule and reagents useful for enabling said interaction to result in amplification of said nucleic acid target. Further compartments may also be included, for example, to receive biological or non-biological samples.

Further features of the present invention are more fully described in the following non-limiting examples.

Example 1

Oligoanayser 3.1—Settings, Assumptions and Limitations (Downloaded from IDT)

Melting Temperature Settings

Target Type DNA

- OLIGO CONC 0.25 UM
- $Na^+$ CONC 50 mM monovalent salt
- $Mg^{++}$ CONC 5 mM divalent salt
- dNTPs CONC 0.3 mM nucleotide triphosphate Melting Temperature Assumptions and Limitations

- Predictions are accurate for oligos from 8 to 60 bases in length, in neutral buffered solutions (pH 7-8) with monovalent cation ($Na^+$) concentrations from 1.2 M down to 1.5 mM, divalent cation ($Mg^{++}$) concentrations from 600 mM down to 0.01 mM, and triphosphates (dNTPs) concentrations up to 120% of the divalent cation concentration.
- Oligo concentration is assumed to be significantly larger (at least 6×) than concentration of the complementary target, which is true in majority of molecular biology experiments. If this is not a case, concentration of the target cannot be ignored and you should enter in the box, Oligo Conc=[strand1]−[strand2]/2 when [strand1]>[strand2]

Oligo Conc=([strand1]+[strand2])/4 when [strand1]=[strand2]

Melting Temperature Accuracy and Models: (Oligo/Template)

| | |
|---|---|
| DNA/DNA | +/−1.4 °C (Allawi '97) |
| LNA/DNA | +/−2.0 °C (McTigue '04, Owczarzy, 2011) |
| RNA/DNA | +/−2.7 °C (Sugimoto '95) |
| DNA/RNA | +/−2.7 °C (Sugimoto '95) |
| RNA/RNA | +/−1.3 °C (Xia '98) |
| Divalent cation correction | +/−0.5 °C (Owczarzy '08) |
| Triphosphate correction | +/−0.0 °C (Owczarzy '08) |
| Monovalent cation correction | +/−2.0 °C (Owczarzy '04) |

Consecutive LNA bases hybridized to a DNA template use a model from Owczarzy '11. In the absence of empirical data, LNA bases on an RNA template assume RNA values, and predictions are therefore less accurate.

Non-consecutive LNA bases hybridized to a DNA template use a model from McTigue '04. Consecutive LNA bases on a DNA template and any LNA bases on an RNA template assume RNA energetic parameters and predictions are therefore less accurate.

Effects of chemical modifications are neglected except when the modification contains a base, e.g., 5-Methyl dC, Internal Fluorescein dT. Energetic effects of these modifications are only approximated.

Example 2

Guidelines for Primer Design

The 3' End
- the last base to be an A/T
- preferably the last 2 bases to be A/T
- can have A/T as the base for up to the last 4 bases. If more than this there is the risk that the primer will not perform as efficiently.
- no more than 2 G/C in the last 6 bases.

Design if Using 2 N Regions
- the primer will be directed to part or all of N1, all of D, and part or all of N2.
- It may be advantageous to include up to 4 bases 5' to N1 and/or 1-3 bases 3' to N2. This takes advantage of the semi-unique V-N1 and N2-J junctions and any A/T bases offered by J.
- If the Tm of the primer is too high, greater than 74° C., one or more N bases can be inserted into the D region to lower the effective Tm.

Design if Using One N Region

Only one N region will be available in the presence of V-N-J or a partial D-N-J rearrangement. Occasionally, even if 2 N regions are available, it may be decided to use only one, particularly if it is long, comprises a favourable heterogeneous sequence of bases and enables a good 3' end to be designed.
- If the N region is followed by a D region, it is usually advantageous to extend the primer 4-6 bases into the D region, particularly if this improves the 3' end. This takes advantage of the semi-unique N-D junction.
- If the N region is followed by the J region, it is usually advantageous to extend the primer 1-3 bases into the J region, occasionally further if one is searching for A/T at the 3' end. However, particularly in this situation, it is important to test several different primers.

Annealing Temperature

The annealing temperature for use in the PCR depends on the Tm of the primer. Guidelines are
- Tm=69-72, annealing temperature=72.
- Tm=72-74, annealing temperature=75
- Tm >74, annealing temperature=75 but consider the use of N bases.

The temperature finally used in practice will be determined by how the primer performs during testing of a range of annealing temperatures.

Note

The above are only guidelines and for most patients it is advisable to synthesise and test more than one candidate primer.

Testing of the Primer

1. Determining Amplification Efficiency and Specificity

One or several primers are synthesised for each patient. Using a gradient of annealing temperatures, each primer is tested for its ability to amplify from leukaemic DNA and for its failure to amplify from nonleukaemic DNA.

Below is shown one example

| 73 | 72.3 | 70.8 | 68.3 | 65.1 | 62.6 | 60.9 | 60 |
|---|---|---|---|---|---|---|---|
| 32.41 | 32.46 | 32.71 | 32.34 | N/A | N/A | N/A | N/A |
| 33.16 | 33.01 | 32.89 | 32.58 | N/A | N/A | N/A | N/A |

The top row shows the range of annealing temperatures; the next 2 rows show the Ct values observed with testing 2 different primers. The 4 cells to the left show the results of amplifying from 400 μg of leukaemic DNA and the 4 cells to the right show the results of amplifying from 1 μg of nonleukaemic DNA. The 2 primers amplified well with annealing temperatures of 68.3-73° C. but did not produce non-specific amplification. Another example, using a slightly different temperature range, is shown below.

| Do | Pbl | Do | Pbl | Do | Pbl | Do | Pbl |
|---|---|---|---|---|---|---|---|
| 75 | 74.6 | 73.9 | 72.5 | 70.8 | 69.4 | 68.5 | 68 |
| 35.80 | NA | 32.98 | NA | 33.20 | NA | 33.20 | NA |

The top row shows the DNA being tested. Do is 400 μg of leukaemic DNA, Pbl is 1 μg of nonleukaemic DNA. The $2^{nd}$ row is the annealing temperature and the $3^{rd}$ row is the observed Ct value. The primer used had a predicted Ct value of 69.5° C. It can be seen that it worked well at an annealing temperature of 73.9 and below, but sub-optimally at an annealing temperature of 75. It did not produce nonspecificity at any annealing temperature.

2. The selected primer is finally tested to ensure that its ability to amplify the rearranged target gene in the leukaemic DNA is not inhibited by the concomitant presence of nonleukaemic DNA.

An example of a test is shown below. The presence of either 500 ng or 1 μg of nonleukaemic DNA made no difference to the CT observed with 400 μg of leukaemic DNA. No amplification was observed with 500 ng of nonleukaemic DNA alone or with the water control

| | |
|---|---|
| Do | 32.89 |
| Do + 500 ng | 32.9 |
| Do + 1 μg | 32.78 |
| 500 ng | N/A |
| water | N/A |

Example 3

Examples of Patient Aso Primers, Sequences, Tm and Specificity

| SEQ ID NO | patient/primer | primer sequence VorV N D N J | Tm | pos/ total |
|---|---|---|---|---|
| 20 | 2-12 | Gatttggacctctaactgggcgctga | 70.5 | 0/20 |
| 21 | 13-12 singleD | Gccccggcctggggattg | 71.6 | 0/30 |
| 22 | 14-15 single1 | **Ggtggcatgaccccacgctctt** | 71.8 | 0/20 |
| 23 | 19-15J6single | CCCTC TCT TTT GGA GTG GTT ATT CCCTCTA | 69.3 | 0/20 |
| 24 | 23-15 single A | GTGCGAGAtt**t**aattttaatggcccggatgtac | 70.1 | 0/20 |
| 25 | 23-15 single B | GCGAGAtttaattttaatggcccggatgtactttg | 70.3 | 0/20 |
| 26 | 24-15 TCR single 2 | GGCGGGTCGGGGGGTAGA | 71.2 | 0/20 |
| 27 | 31-17 1 single 1 | TTCCCAGTAAATAGGATATTGTACTGGTGGTGTATGCTATTGGGCGTA | 74.9 | 0/20 |
| 28 | 31-17 TCR single1 | CTAGCGGGGGGGATGGTGATACAAT | 71..0 | 0/20 |
| 29 | 34-17single1 | CTCATGGGCTCGTCCTGGGTACTA | 69.4 | 1/20 |
| 30 | 37-16singleG | tcctactgtgtgactacgagccctctac | 70.0 | 0/20 |
| 31 | 41-17 single | CTG TGC TAA CTG GGG AGG GGC TA | 70.8 | 3/20 |
| 32 | 42-17single | **CTGT**GCGAGACA AGAA GGAACC GAAG AC | 70.5 | 0/20 |
| 33 | RAH056 single | CTG TGCTAACTGGGAAGGGGCACT | 70.9 | 2/20 |
| 34 | 45-16 single 1 | GAGATAGCCCCTTAGCAGTGGCACCT | 71.6 | 0/20 |
| 35 | 45-17single3 | AG ATCAAGGT GGGTATTGTAGTGGTGGTAGCTGC CTTACACAG | 74.7 | 0/20 |
| 36 | 52-16single | **GA**TAGGAATTACTATGATAGTAGTGGTCCGCTAGGGTCCGTT | 72.9 | 0/20 |
| 37 | 54-16single | CCCGTGGGTGTGGAGCTGCTTACCTAGCCT | 76.2 | 0/20 |
| 38 | 55-16 outer | GTCCCCTGGGCCTACCTCAAGTTAATATA | 69.2 | 0/20 |
| 39 | 68-17 | GCAAAAGATGGCCCCTTACTATGATAAGGGGTAA | 71.2 | 0/20 |
| 40 | 69-16 single | gggagagatcagtgggggggt | 70.1 | 0/20 |
| 41 | 71-16single | ctgtgcacggtctaggggtacctta | 69.5 | 0/20 |
| 42 | 72-16 single | gatctcg**A**taTttTgaCtgGttAttagtccccaacgagta | 71.3 | 0/20 |
| 43 | 93-11singleA | gatctcttgataggagttcggggagttattttggccccccaaagcgat | 77.3 | 0/20 |
| 44 | 108-17 | CTGTGCTAACTGGGGAAGCTGGACT | 70.5 | 0/20 |
| 45 | 109/17single1 | GGTGAGCTCAAATCCGGGGGCATATT | 71.1 | 0/20 |
| 46 | 110-17 single | CAGCTGCTTATAACCGCGTAGACCTATTTT | 69.1 | 0/20 |
| 47 | 111-17 TCRsingleJ2.5 | CTTAGCGGTGGCGAGGGAGATCCAA | 71.9 | 0/20 |
| 48 | 112-17single J5 | GAAGGTAGCTGCTACGATTAGTGCGTCCGCCT | 74.4 | 0/20 |
| 49 | 114-17 single 2 | GGGTTACATTTGGGGGAGTTATCGTTTTCCGGGA | 73.6 | 0/20 |
| 50 | 115-17 single | CCCTTTTCCCTACGATTTTTGGAGTGGTTACAGGGCTGGCTA | 76.1 | 0/20 |
| 51 | 15-282 | **TCTGAGGCTATAGGAGTGGTGGAGGGGCCCTTT** | 76 | 0/20 |
| 52 | 15-283 single | **GAGA CGGGTCTATGATACTAGTGGACCCGC CTTT** | 73.3 | 0/20 |
| 53 | 15-284single | GAGAGGTTATTGCAGTGGTGGCAGTTGCTCCTCAAGGGGGGGGTTTT T | 79.2 | 0/20 |
| 54 | 15-285 single | **GAGGAACCCTAGTGGGAGCTACTGATCGGATGCTTTCT** | 74.9 | 0/20 |

-continued

| SEQ ID NO | patient/primer | primer sequence VorV N D N J | Tm | pos/ total |
|---|---|---|---|---|
| 55 | 15-286 | **GCGA AATTGGGGGATAGTGGGAGCTGGTC TGA** | 74.8 | 0/20 |
| 56 | 90-17 | TTCGAATCGGCGTCTGAGGGCCCAAT | 73.8 | 0/20 |
| 57 | 67-16 | GGACAGATTACTATGGTTCGGGGAGTTAAATAGGGCT | 72.4 | 0/20 |
| 58 | 37/18 single 1 | GACTGGTTATTAACTCACCTCGCATTTTGTGTTGAA | 71 | |
| 59 | 37/18 single 2 | CTGCTCTTGTTGGAGCAGGGGTT | 69.8 | |
| 60 | 37/18 single 3 | GGATATTGTAGTAGTACCAGCTGCTGCTCTTGTT | 70.9 | |

Assessment of specificity involved amplification of 20 wells each containing 1 µg of non-leukaemic DNA pooled from 5 normal individuals. Nonspecific amplification was seen with only 3 of 34 primers. Amplification from 1 of 20 wells is equivalent to an MRD level of 2.3× 10-7.

Example 4

Gradient—for Testing Primers

Diagnostic DNA at 200 pg/µl add 2 µl/tube need 35 µl/primer pbl DNA at 250 ng/µl add 2 µl/tube need 35 µl/primer D0 primer rows A C E G PBL same primer rows B D F H

| | 1 | 106 |
|---|---|---|
| H2O | 12.48 | 1322.88 |
| 10X Buffer | 2 | 212 |
| 50 mM $MgCl_2$ | 2 | 212 |
| 10 mM dNTP | 0.6 | 63.6 |
| syto 82 1/100 | 0.2 | 21.2 |
| Reverse @ 50 uM | 0 | 0 |
| IgH J @ 20 uM | 0.16 | 16.96 |
| Platinum taq 5 U/ul | 0.16 | 16.96 |
| | 17.6 | 1865.6 |

Divide into 12 at 8.5×17.6=149.6 µl and add 2 µl reverse primer, 2 µl forward single primer @ 50 µM and 17 µl DNA at 200 pg/µl or pbl at 250 ng/µl Aliquot 20 µl into wells, seal and run the following protocol Run on PCR machine CFX 91° C. 3 mins.×1:

97° C. 15 secs, 68-75° C. 30 secs, ×5 cycles

96° C. 15 secs, 68-75° C. 30 secs, ×5 cycles

94° C. 15 secs, 68-75° C. 30 secs×35 cycles

Melt 65° C.-95° C.

This method is for testing the amplification efficiency and specificity of the primers at a range of annealing temperatures.

1 and 106 refer to component volumes for a single well or for the total wells respectively

Example 5

Appendix 5. Worksheet 4: To Make Up Mixes for Quantification Using Single Primer Patient Diagnostic DNA at 1 ng/µl Pbl DNA need 120 µl at 250 ng/µl 4 µl/tube Dilutions in MR Tubes

| | |
|---|---|
| From 1 ng/ul | 3 ul + 27 ul FG3 0.1 ng/ul |
| From 0.1 ng/u1 | 2 ul + 18 ul FG3 0.01 ng/ul |

Need pbl 250 ng/µl to make up mixes to add 20 µl/tube

| | No. Tubes | | pat DNA µl | pbl µl | H2O µl to 20 µl/tube |
|---|---|---|---|---|---|
| 1 × $10^3$ | 2.25 | 1 ng | 2.25 | 9 at 250 ng/µl | 33.75 |
| 1 × $10^{-4}$ | 2.25 | 0.1 ng | 2.25 | 9 at 250 ng/µl | 33.75 |
| 2 × $10^{-5}$ | 3.25 | 0.01 ng | 6.5 | 13 at 250 ng/µl | 42.25 |
| Pbl | 21 | — | — | 84 at 250 ng/µl | 336 |

| | | Copies/tube |
|---|---|---|
| $10^{-3}$ | 1 ng/1 µg | 151 |
| $10^{-4}$ | 0.1 ng/l µg | 15.1 |
| 2 × $10^{-5}$ | 0.01/1 µg | 3.00 |

Example 6

Quantification Using Single Primer for 2 Samples, 2 Tubes and 5 Tubes

| | 1 | 41 |
|---|---|---|
| H2O | 16 | 656 |
| 10X Buffer | 5 | 205 |
| $MgCl_2$ | 5 | 205 |
| TTP | 1.5 | 61.5 |
| single primer 500 ng | 0.4 | 16.4 |
| syto 82 | 0.5 | 20.5 |
| Reverse 500 ng/µl | 0.4 | 16.4 |
| igHJ probe | 0.4 | 16.4 |
| Platinum taq 5 U/ul | 0.8 | 32.8 |
| | 30 | 1230 |

| | | |
|---|---|---|
| Mix 1) 2) $10^{-3}$ $10^{-4}$ 2 tubes each | 30 ul PCR mix | 1-4 |
| | 20 ul DNA mix | |
| | 50 µl | |
| Mix 3) 10-5 3.25 tubes | 97.5 µl PCR Mix | 5-7 |
| | 65 µl DNA mix | |
| | 162.5 µl | |

-continued

| | | |
|---|---|---|
| Mix 4) Sample 2.2 tubes | 66 µl PCR Mix | 8-9 |
| | µl DNA | |
| | µl water | |
| | 110 µl | |
| Mix 5) Sample 5.25 tubes | 157.5 µl PCR Mix | 10-14 |
| | µl DNA | |
| | µl water | |
| | 262.5 µl | |
| Mix 6) pbl DNA 21 tubes | 630 µl mix | 15-34 |
| | 420 µl DNA | |
| | 1050 µl | |
| Mix 7) +ve control X2 tubes | 30 ul mix | 35-36 |
| | 10 ul 0.1 ng/ul D0 in TE | |
| | 10 µl water | |
| | 50 ul x2 | |
| Mix 8) negative X2 tubes | 30 ul mix | 37-38 |
| | 20 ul H2O | |
| | 50 ul x2 | |

Run: 91° C. 3 Mins

97° C., 15 sec; 72° C., 30 sec×5 cycles

96° C., 15 sec; 72° C., 30 sec×5 cycles,

94° C., 15 sec; 72° C., 30 sec×35 cycles

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Brisco, M. J., Bartley, P. A., and Morley, A. A. Antisense PCR: A simple and robust method for performing nested single-tube PCR. Analytical Biochemistry 2011; 409:176-182

Bruggemann M, van der Velden V H, Raff T, Droese J, Ritgen M, Pott C, et al. Rearranged T-cell receptor beta genes represent powerful targets for quantification of minimal residual disease in childhood and adult T-cell acute lymphoblastic leukemia. Leukemia. 2004; 18 (4): 709-19.

Morley A A, Latham S, Brisco M J, Sykes P J, Sutton R, Hughes E, et al. Sensitive and specific measurement of minimal residual disease in acute lymphoblastic leukemia. J Mol Diagn. 2009; 11 (3): 201-10.

Nakao M, Janssen J W, Flohr T, Bartram C R. Rapid and reliable quantification of minimal residual disease in acute lymphoblastic leukemia using rearranged immunoglobulin and T-cell receptor loci by LightCycler technology. Cancer Res. 2000; 60 (12): 3281-9.

Pongers-Willemse M J, Seriu T, Stolz F, d'Aniello E, Gameiro P, Pisa P, et al. Primers and protocols for standardized detection of minimal residual disease in acute lymphoblastic leukemia using immunoglobulin and T cell receptor gene rearrangements and TAL1 deletions as PCR targets: report of the BIOMED-1 CONCERTED ACTION: investigation of minimal residual disease in acute leukemia. Leukemia. 1999; 13 (1): 110-8.

van der Velden V H, Boeckx N, van Wering E R, van Dongen J J. Detection of minimal residual disease in acute leukemia. J Biol Regul Homeost Agents. 2004; 18 (2): 146-54.

van der Velden V H, Panzer-Grumayer E R, Cazzaniga G, Flohr T, Sutton R, Schrauder A, et al. Optimization of PCR-based minimal residual disease diagnostics for childhood acute lymphoblastic leukemia in a multi-center setting. Leukemia. 2007; 21 (4): 706-13.

van der Velden V H, van Dongen J J. MRD detection in acute lymphoblastic leukemia patients using Ig/TCR gene rearrangements as targets for real-time quantitative PCR. Methods Mol Biol. 2009; 538:115-50.

van der Velden V H, Wijkhuijs J M, Jacobs D C, van Wering E R, van Dongen J J. T cell receptor gamma gene rearrangements as targets for detection of minimal residual disease in acute lymphoblastic leukemia by real-time quantitative PCR analysis. Leukemia. 2002; 16 (7): 1372-80.

van der Velden V H, Willemse M J, van der Schoot C E, Hahlen K, van Wering E R, van Dongen J J. Immunoglobulin kappa deleting element rearrangements in precursor-B acute lymphoblastic leukemia are stable targets for detection of minimal residual disease by real-time quantitative PCR. Leukemia. 2002; 16 (5): 928-36.

van der Velden VHJ, Noordijk R, Brussee M, Hoogeveen P, Homburg C, de Haas V, C. van der Schoot E, van Dongen JJM. Minimal residual disease diagnostics in acute lymphoblastic leukaemia: Impact of primer characteristics and size of junctional regions. British Journal of Haematology, 2014, 164, 451-464

Verhagen O J, Willemse M J, Breunis W B, Wijkhuijs A J, Jacobs D C, Joosten S A, et al. Application of germline IGH probes in real-time quantitative PCR for the detection of minimal residual disease in acute lymphoblastic leukemia. Leukemia. 2000; 14 (8): 1426-35.

The invention claimed is:

1. A method of amplifying an immunoglobulin (Ig) or T cell receptor (TCR) nucleic acid region which is characterised by a specific rearrangement of two or more V, D or J gene segments said method comprising contacting a nucleic acid sample of interest with two primers in a single reaction wherein the reaction is not a multiplex or nested PCR and said two primers are one forward primer and one reverse primer directed to said specific rearrangement, and quantitatively amplifying said nucleic acid sample wherein:

(i) both the forward and reverse primers exhibit a Tm of 67° C. to 76° C.;

(ii) said method uses an annealing temperature of at least 70° C.;

(iii) one or more A and/or T nucleotides are included at the 3' end of each of said forward and reverse primers; and wherein the method exhibits greater amplification sensitivity compared to a method lacking (i) to (iii).

2. The method according to claim 1 wherein said forward primer is an allele specific oligonucleotide (ASO) primer.

3. The method according to claim 1 wherein said nucleic acid region is a DNA region.

4. The method according to claim 1 wherein said forward and reverse primers of step (i) have a Tm of 68-76° C. or 69-74° C.

5. The method according to claim 1 wherein said annealing temperature is 70° C., 71° C., 72° C., 73° C., 74° C., 75° C., or 76° C.

6. The method according to claim 1 wherein said forward and reverse primers of step (i) have a Tm of 67° C.-76° C. and/or said annealing temperature is 70° C.-83° C.

7. The method according to claim 1 wherein said forward and reverse primers have a Tm of 69° C. to 76° C. and said annealing temperature is 70° C. to 78° C.

8. The method according to claim 1 wherein said forward and reverse primers have a Tm of 69° C. to 76° C. and said annealing temperature is 72° C. to 75° C.

9. The method according to claim 1 wherein said forward and reverse primers have a Tm of 72° C. to 76° C. and said annealing temperature is 75° C.

10. The method according to claim 1 wherein at least one of said primers comprises hybridisation subregions directed to at least two N gene segments of the rearranged V, D and J gene segments.

11. The method according to claim 10 wherein said V, D, J rearrangement is a partial rearrangement.

12. The method according to claim 11 wherein said partial V, D, J rearrangement is a DNJ or VNJ rearrangement which also comprises at least one N region within the D, J or V gene segment.

13. The method according to claim 12 wherein said at least two N gene segments are the N gene segments of the $DN_2$, $N_2J$, $DN_2J$, $VN_1$, $N_2J$, $VN_2J$, $N_1D$ or $VN_1D$, rearrangements and at least one N region within the relevant D, J or V gene segment.

14. The method according to claim 12 wherein said at least two N gene segments are the N gene segments of the $N_1DN_2$, $VN_1DN_2$ or $N_1DN_2J$ rearrangements.

15. The method according to claim 10 wherein said V, D, J rearrangement is a complete VDJ rearrangement.

16. The method according to claim 15 wherein said at least two N gene segments are the N gene segments of the $N_1DN_2$ rearrangement.

17. The method according to claim 1 wherein said reverse primer is a primer directed to the J gene segment and said reverse primer comprises at least one A and/or T nucleotide at its 3' end.

18. The method according to claim 1 wherein a primer subregion is modified to substitute one or more of the nucleotides of said subregion with a nucleotide from an N mixture.

19. The method according to claim 18 wherein every fourth nucleotide of said subregion is substituted.

20. The method according to claim 18 wherein a sequence of 3-7 adjacent nucleotides of said subregion are substituted.

21. A method of detecting and/or monitoring a clonal population of cells in a mammal, which clonal cells are characterised by an Ig or TCR nucleic acid region which is characterised by the rearrangement of two or more V, D or J gene segments, said method comprising performing the amplification method according to claim 1 and detecting said amplified product.

22. The method according to claim 21 further comprising diagnosing or monitoring a disease condition characterised by a clonal population of cells which are characterised by an Ig or TCR nucleic acid region comprising the rearrangement of two or more V, D or J gene segments.

23. The method according to claim 22 wherein said clonal cells are a population of clonal lymphoid cells.

24. The method according to claim 23 wherein said disease condition is a neoplasia or lymphoid neoplasia.

25. The method according to claim 24 wherein said lymphoid neoplasia is leukaemia, lymphoma or myeloma.

26. The method according to claim 21 wherein said method is used to detect minimum residual disease.

27. The method according to claim 1 wherein said sample is human sample.

* * * * *

SEQUENCE LISTING

<160> NUMBER OF SEQ ID NOS: 60

<210> SEQ ID NO 1
<211> LENGTH: 30
<212> TYPE: DNA
<213> ORGANISM: Artificial Sequence
<220> FEATURE:
<223> OTHER INFORMATION: AAMJ1b

<400> SEQUENCE: 1
ctttgctgag cacctgtccc caagtctgaa 30

```
<210> SEQ ID NO 2
<211> LENGTH: 23
<212> TYPE: DNA
<213> ORGANISM: Artificial Sequence
<220> FEATURE:
<223> OTHER INFORMATION: AAMJ2

<400> SEQUENCE: 2

aggccggctg cagaccccag ata                                              23


<210> SEQ ID NO 3
<211> LENGTH: 26
<212> TYPE: DNA
<213> ORGANISM: Artificial Sequence
<220> FEATURE:
<223> OTHER INFORMATION: AAMJ3c

<400> SEQUENCE: 3

cccccggaca ttatctccca gctcca                                           26


<210> SEQ ID NO 4
<211> LENGTH: 34
<212> TYPE: DNA
<213> ORGANISM: Artificial Sequence
<220> FEATURE:
<223> OTHER INFORMATION: AAMJ4c

<400> SEQUENCE: 4

gcttatttcc ccccaaaaat gcagcaaaac cctt                                  34


<210> SEQ ID NO 5
<211> LENGTH: 32
<212> TYPE: DNA
<213> ORGANISM: Artificial Sequence
<220> FEATURE:
<223> OTHER INFORMATION: AAMJ5c

<400> SEQUENCE: 5

cctccaaaat gcctccaaga ctctgaccct ga                                    32


<210> SEQ ID NO 6
<211> LENGTH: 31
<212> TYPE: DNA
<213> ORGANISM: Artificial Sequence
<220> FEATURE:
<223> OTHER INFORMATION: AAMJ6c

<400> SEQUENCE: 6

aggaaacccc acaggcagta gcagaaaaca a                                     31


<210> SEQ ID NO 7
<211> LENGTH: 31
<212> TYPE: DNA
<213> ORGANISM: Artificial Sequence
<220> FEATURE:
<223> OTHER INFORMATION: TCR1.1b

<400> SEQUENCE: 7

ttccctgtga cggatctgca aaagaacctg a                                     31


<210> SEQ ID NO 8
<211> LENGTH: 31
<212> TYPE: DNA
<213> ORGANISM: Artificial Sequence
<220> FEATURE:
<223> OTHER INFORMATION: TCR1.2b
```

<400> SEQUENCE: 8
ccctcctaga gacccccagc cttacctaca a 31

<210> SEQ ID NO 9
<211> LENGTH: 31
<212> TYPE: DNA
<213> ORGANISM: Artificial Sequence
<220> FEATURE:
<223> OTHER INFORMATION: TCR1.3b

<400> SEQUENCE: 9
caagttccca gctgtccagc cttgacttac t 31

<210> SEQ ID NO 10
<211> LENGTH: 39
<212> TYPE: DNA
<213> ORGANISM: Artificial Sequence
<220> FEATURE:
<223> OTHER INFORMATION: TCR1.4b

<400> SEQUENCE: 10
ccaggaactc cgaccttatg atacactatc ccgaaagaa 39

<210> SEQ ID NO 11
<211> LENGTH: 34
<212> TYPE: DNA
<213> ORGANISM: Artificial Sequence
<220> FEATURE:
<223> OTHER INFORMATION: TCR1.5b

<400> SEQUENCE: 11
atggccatac caccctgatt ctgcaactta ccta 34

<210> SEQ ID NO 12
<211> LENGTH: 28
<212> TYPE: DNA
<213> ORGANISM: Artificial Sequence
<220> FEATURE:
<223> OTHER INFORMATION: TCR1.6b

<400> SEQUENCE: 12
gagtcaagag tggagccccc atacctgt 28

<210> SEQ ID NO 13
<211> LENGTH: 27
<212> TYPE: DNA
<213> ORGANISM: Artificial Sequence
<220> FEATURE:
<223> OTHER INFORMATION: TCR2.1b

<400> SEQUENCE: 13
cacctggagc ccccttctta cctagca 27

<210> SEQ ID NO 14
<211> LENGTH: 21
<212> TYPE: DNA
<213> ORGANISM: Artificial Sequence
<220> FEATURE:
<223> OTHER INFORMATION: TCR2.2b

<400> SEQUENCE: 14
cggagcccca accgcctcct t 21

<210> SEQ ID NO 15
<211> LENGTH: 22

<212> TYPE: DNA
<213> ORGANISM: Artificial Sequence
<220> FEATURE:
<223> OTHER INFORMATION: TCR2.3b

<400> SEQUENCE: 15
ggagccccgc ttaccgagca ct 22

<210> SEQ ID NO 16
<211> LENGTH: 16
<212> TYPE: DNA
<213> ORGANISM: Artificial Sequence
<220> FEATURE:
<223> OTHER INFORMATION: TCR2.4b

<400> SEQUENCE: 16
ccggcggccc cagctt 16

<210> SEQ ID NO 17
<211> LENGTH: 20
<212> TYPE: DNA
<213> ORGANISM: Artificial Sequence
<220> FEATURE:
<223> OTHER INFORMATION: TCR2.5b

<400> SEQUENCE: 17
gcgctcaccg agcaccagga 20

<210> SEQ ID NO 18
<211> LENGTH: 25
<212> TYPE: DNA
<213> ORGANISM: Artificial Sequence
<220> FEATURE:
<223> OTHER INFORMATION: TCR2.6b

<400> SEQUENCE: 18
cgcgaaaact cacccagcac ggtca 25

<210> SEQ ID NO 19
<211> LENGTH: 23
<212> TYPE: DNA
<213> ORGANISM: Artificial Sequence
<220> FEATURE:
<223> OTHER INFORMATION: TCR2.7d

<400> SEQUENCE: 19
ggaaggtggg gagacgcccg aat 23

<210> SEQ ID NO 20
<211> LENGTH: 26
<212> TYPE: DNA
<213> ORGANISM: artificial sequence
<220> FEATURE:
<223> OTHER INFORMATION: Primer

<400> SEQUENCE: 20
gatttggacc tctaactggg cgctga 26

<210> SEQ ID NO 21
<211> LENGTH: 18
<212> TYPE: DNA
<213> ORGANISM: artificial sequence
<220> FEATURE:
<223> OTHER INFORMATION: Primer

<400> SEQUENCE: 21
gccccggcct ggggattg 18

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ggtggcatga ccccacgctc tt 22

<210> SEQ ID NO 23
<211> LENGTH: 30
<212> TYPE: DNA
<213> ORGANISM: artificial sequence
<220> FEATURE:
<223> OTHER INFORMATION: Primer

<400> SEQUENCE: 23
ccctctcttt tggagtggtt attccctcta 30

<210> SEQ ID NO 24
<211> LENGTH: 33
<212> TYPE: DNA
<213> ORGANISM: Artificial Sequence
<220> FEATURE:
<223> OTHER INFORMATION: Primer

<400> SEQUENCE: 24
gtgcgagatt taattttaat ggcccggatg tac 33

<210> SEQ ID NO 25
<211> LENGTH: 35
<212> TYPE: DNA
<213> ORGANISM: artificial sequence
<220> FEATURE:
<223> OTHER INFORMATION: Primer

<400> SEQUENCE: 25
gcgagattta attttaatgg cccggatgta ctttg 35

<210> SEQ ID NO 26
<211> LENGTH: 18
<212> TYPE: DNA
<213> ORGANISM: artificial sequence
<220> FEATURE:
<223> OTHER INFORMATION: Primer

<400> SEQUENCE: 26
ggcgggtcgg ggggtaga 18

<210> SEQ ID NO 27
<211> LENGTH: 48
<212> TYPE: DNA
<213> ORGANISM: artificial sequence
<220> FEATURE:
<223> OTHER INFORMATION: Primer

<400> SEQUENCE: 27
ttcccagtaa ataggatatt gtactggtgg tgtatgctat tgggcgta 48

<210> SEQ ID NO 28
<211> LENGTH: 25
<212> TYPE: DNA
<213> ORGANISM: artificial sequence
<220> FEATURE:
<223> OTHER INFORMATION: Primer

<400> SEQUENCE: 28
ctagcggggg ggatggtgat acaat 25

<210> SEQ ID NO 29
<211> LENGTH: 24
<212> TYPE: DNA
<213> ORGANISM: artificial sequence
<220> FEATURE:
<223> OTHER INFORMATION: Primer

<400> SEQUENCE: 29
ctcatgggct cgtcctgggt acta 24

<210> SEQ ID NO 30
<211> LENGTH: 28
<212> TYPE: DNA
<213> ORGANISM: artificial sequence
<220> FEATURE:
<223> OTHER INFORMATION: Primer

<400> SEQUENCE: 30
tcctactgtg tgactacgag ccctctac 28

<210> SEQ ID NO 31
<211> LENGTH: 23
<212> TYPE: DNA
<213> ORGANISM: artificial sequence
<220> FEATURE:
<223> OTHER INFORMATION: Primer

<400> SEQUENCE: 31
ctgtgctaac tggggagggg cta 23

<210> SEQ ID NO 32
<211> LENGTH: 28
<212> TYPE: DNA
<213> ORGANISM: artificial sequence
<220> FEATURE:
<223> OTHER INFORMATION: Primer

<400> SEQUENCE: 32
ctgtgcgaga caagaaggaa ccgaagac 28

<210> SEQ ID NO 33
<211> LENGTH: 24
<212> TYPE: DNA
<213> ORGANISM: artificial sequence
<220> FEATURE:
<223> OTHER INFORMATION: Primer

<400> SEQUENCE: 33
ctgtgctaac tgggaagggg cact 24

<210> SEQ ID NO 34
<211> LENGTH: 26
<212> TYPE: DNA
<213> ORGANISM: artificial sequence
<220> FEATURE:
<223> OTHER INFORMATION: Primer

<400> SEQUENCE: 34
gagatagccc cttagcagtg gcacct 26

<210> SEQ ID NO 35
<211> LENGTH: 43
<212> TYPE: DNA
<213> ORGANISM: artificial sequence
<220> FEATURE:
<223> OTHER INFORMATION: Primer

<400> SEQUENCE: 35
agatcaaggt gggtattgta gtggtggtag ctgccttaca cag 43

<210> SEQ ID NO 36
<211> LENGTH: 42
<212> TYPE: DNA
<213> ORGANISM: artificial sequence
<220> FEATURE:
<223> OTHER INFORMATION: Primer

<400> SEQUENCE: 36
gataggaatt actatgatag tagtggtccg ctagggtccg tt 42

<210> SEQ ID NO 37
<211> LENGTH: 30
<212> TYPE: DNA
<213> ORGANISM: artificial sequence
<220> FEATURE:
<223> OTHER INFORMATION: Primer

<400> SEQUENCE: 37
cccgtgggtg tggagctgct tacctagcct 30

<210> SEQ ID NO 38
<211> LENGTH: 29
<212> TYPE: DNA
<213> ORGANISM: artificial sequence
<220> FEATURE:
<223> OTHER INFORMATION: Primer

<400> SEQUENCE: 38
gtcccctggg cctacctcaa gttaatata 29

<210> SEQ ID NO 39
<211> LENGTH: 34
<212> TYPE: DNA
<213> ORGANISM: artificial sequence
<220> FEATURE:
<223> OTHER INFORMATION: Primer

<400> SEQUENCE: 39
gcaaaagatg gcccccttact atgataaggg gtaa 34

<210> SEQ ID NO 40
<211> LENGTH: 21
<212> TYPE: DNA
<213> ORGANISM: artificial sequence
<220> FEATURE:
<223> OTHER INFORMATION: Primer

<400> SEQUENCE: 40
gggagagatc agtgggggggg t 21

<210> SEQ ID NO 41
<211> LENGTH: 25
<212> TYPE: DNA
<213> ORGANISM: artificial sequence
<220> FEATURE:
<223> OTHER INFORMATION: Primer

<400> SEQUENCE: 41
ctgtgcacgg tctaggggta cctta 25

<210> SEQ ID NO 42
<211> LENGTH: 40
<212> TYPE: DNA
<213> ORGANISM: artificial sequence
<220> FEATURE:
<223> OTHER INFORMATION: Primer

<400> SEQUENCE: 42
gatctcgata ttttgactgg ttattagtcc ccaacgagta 40

<210> SEQ ID NO 43
<211> LENGTH: 48
<212> TYPE: DNA
<213> ORGANISM: artificial sequence
<220> FEATURE:
<223> OTHER INFORMATION: Primer

<400> SEQUENCE: 43
gatctcttga taggagttcg gggagttatt ttggcccccc aaagcgat 48

<210> SEQ ID NO 44
<211> LENGTH: 25
<212> TYPE: DNA
<213> ORGANISM: artificial sequence
<220> FEATURE:
<223> OTHER INFORMATION: Primer

<400> SEQUENCE: 44
ctgtgctaac tggggaagct ggact 25

<210> SEQ ID NO 45
<211> LENGTH: 26
<212> TYPE: DNA
<213> ORGANISM: artificial sequence
<220> FEATURE:
<223> OTHER INFORMATION: Primer

<400> SEQUENCE: 45
ggtgagctca aatccggggg catatt 26

<210> SEQ ID NO 46
<211> LENGTH: 30
<212> TYPE: DNA
<213> ORGANISM: artificial sequence
<220> FEATURE:
<223> OTHER INFORMATION: Primer

<400> SEQUENCE: 46
cagctgctta taaccgcgta gacctatttt 30

<210> SEQ ID NO 47
<211> LENGTH: 25
<212> TYPE: DNA
<213> ORGANISM: artificial sequence
<220> FEATURE:
<223> OTHER INFORMATION: Primer

<400> SEQUENCE: 47
cttagcggtg gcgagggaga tccaa 25

<210> SEQ ID NO 48

<211> LENGTH: 32
<212> TYPE: DNA
<213> ORGANISM: artificial sequence
<220> FEATURE:
<223> OTHER INFORMATION: Primer

<400> SEQUENCE: 48
gaaggtagct gctacgatta gtgcgtccgc ct 32

<210> SEQ ID NO 49
<211> LENGTH: 34
<212> TYPE: DNA
<213> ORGANISM: artificial sequence
<220> FEATURE:
<223> OTHER INFORMATION: Primer

<400> SEQUENCE: 49
gggttacatt tgggggagtt atcgttttcc ggga 34

<210> SEQ ID NO 50
<211> LENGTH: 42
<212> TYPE: DNA
<213> ORGANISM: artificial sequence
<220> FEATURE:
<223> OTHER INFORMATION: Primer

<400> SEQUENCE: 50
cccttttccc tacgattttt ggagtggtta cagggctggc ta 42

<210> SEQ ID NO 51
<211> LENGTH: 33
<212> TYPE: DNA
<213> ORGANISM: artificial sequence
<220> FEATURE:
<223> OTHER INFORMATION: Primer

<400> SEQUENCE: 51
tctgaggcta taggagtggt ggaggggccc ttt 33

<210> SEQ ID NO 52
<211> LENGTH: 34
<212> TYPE: DNA
<213> ORGANISM: artificial sequence
<220> FEATURE:
<223> OTHER INFORMATION: Primer

<400> SEQUENCE: 52
gagacgggtc tatgatacta gtggacccgc cttt 34

<210> SEQ ID NO 53
<211> LENGTH: 48
<212> TYPE: DNA
<213> ORGANISM: artificial sequence
<220> FEATURE:
<223> OTHER INFORMATION: Primer

<400> SEQUENCE: 53
gagaggttat tgcagtggtg gcagttgctc ctcaaggggg gggttttt 48

<210> SEQ ID NO 54
<211> LENGTH: 38
<212> TYPE: DNA
<213> ORGANISM: artificial sequence
<220> FEATURE:
<223> OTHER INFORMATION: Primer

<400> SEQUENCE: 54
gaggaaccct agtgggagct actgatcgga tgctttct 38

<210> SEQ ID NO 55
<211> LENGTH: 32
<212> TYPE: DNA
<213> ORGANISM: artificial sequence
<220> FEATURE:
<223> OTHER INFORMATION: Primer

<400> SEQUENCE: 55
gcgaaattgg gggatagtgg gagctggtct ga 32

<210> SEQ ID NO 56
<211> LENGTH: 26
<212> TYPE: DNA
<213> ORGANISM: artificial sequence
<220> FEATURE:
<223> OTHER INFORMATION: Primer

<400> SEQUENCE: 56
ttcgaatcgg cgtctgaggg cccaat 26

<210> SEQ ID NO 57
<211> LENGTH: 37
<212> TYPE: DNA
<213> ORGANISM: artificial sequence
<220> FEATURE:
<223> OTHER INFORMATION: Primer

<400> SEQUENCE: 57
ggacagatta ctatggttcg gggagttaaa tagggct 37

<210> SEQ ID NO 58
<211> LENGTH: 36
<212> TYPE: DNA
<213> ORGANISM: artificial sequence
<220> FEATURE:
<223> OTHER INFORMATION: Primer

<400> SEQUENCE: 58
gactggttat taactcacct cgcattttgt gttgaa 36

<210> SEQ ID NO 59
<211> LENGTH: 23
<212> TYPE: DNA
<213> ORGANISM: artificial sequence
<220> FEATURE:
<223> OTHER INFORMATION: Primer

<400> SEQUENCE: 59
ctgctcttgt tggagcaggg gtt 23

<210> SEQ ID NO 60
<211> LENGTH: 34
<212> TYPE: DNA
<213> ORGANISM: artificial sequence
<220> FEATURE:
<223> OTHER INFORMATION: Primer

<400> SEQUENCE: 60
ggatattgta gtagtaccag ctgctgctct tgtt 34